(12) United States Patent
Yaghi et al.

(10) Patent No.: US 9,512,145 B2
(45) Date of Patent: Dec. 6, 2016

(54) POROUS REACTIVE FRAMEWORK

(75) Inventors: Omar M. Yaghi, Los Angeles, CA (US); Alexader U. Czaja, Dirmstein (DE); William Morris, Los Angeles, CA (US); Joseph R. Hunt, Fredericksburg, VA (US); David Kyle Britt, Los Angeles, CA (US); Chain Lee, Monterey Park, CA (US)

(73) Assignees: The Regents of the University of California, Oakland, CA (US); BASF SE, Ludwigshafen (DE)

( * ) Notice: Subject to any disclaimer, the term of this patent is extended or adjusted under 35 U.S.C. 154(b) by 863 days.

(21) Appl. No.: 13/140,408

(22) PCT Filed: Dec. 18, 2009

(86) PCT No.: PCT/US2009/068731
§ 371 (c)(1),
(2), (4) Date: Sep. 6, 2011

(87) PCT Pub. No.: WO2010/080618
PCT Pub. Date: Jul. 15, 2010

(65) Prior Publication Data
US 2011/0319630 A1    Dec. 29, 2011

Related U.S. Application Data

(60) Provisional application No. 61/138,732, filed on Dec. 18, 2008.

(51) Int. Cl.
| | | |
|---|---|---|
| *B01J 20/30* | (2006.01) | |
| *B01J 20/22* | (2006.01) | |
| *B01J 31/16* | (2006.01) | |
| *B01J 31/18* | (2006.01) | |
| *B01J 31/22* | (2006.01) | |
| *C07F 7/00* | (2006.01) | |
| *C07F 3/00* | (2006.01) | |

(52) U.S. Cl.
CPC ..................... *C07F 3/003* (2013.01)

(58) Field of Classification Search
None
See application file for complete search history.

(56) References Cited

U.S. PATENT DOCUMENTS 4,532,225 A   7/1985   Tsao et al.
5,160,500 A   11/1992  Chu et al.
(Continued)

FOREIGN PATENT DOCUMENTS

DE   102005054523 A1   5/2007
EP         1674555 A1   12/2006
(Continued)

OTHER PUBLICATIONS

Morris et al., "Supporting Information for "Crystals as Molecules: Postsynthesis Covalent Functionalization of Zeolitic Imidazolate Frameworks."" J. Am. Chem. Soc. 2008, 130 (38), pp. 12626-12627 (published on Web on Aug. 28, 2008).*

(Continued)

*Primary Examiner* — Daniel Berns
(74) *Attorney, Agent, or Firm* — Joseph R. Baker, Jr.; Gavrilovich, Dodd & Lindsey LLP

(57) ABSTRACT

This disclosure relates to porous frameworks for gas separation, sensing and drug/biomolecule delivery. More particularly, the disclosure relates to reactive porous frameworks for functionalization.

18 Claims, 26 Drawing Sheets

(56) References Cited

U.S. PATENT DOCUMENTS

| | | | |
|---|---|---|---|
| 5,208,335 A | 5/1993 | Ramprasad et al. | |
| 5,648,508 A | 7/1997 | Yaghi et al. | |
| 5,733,505 A | 3/1998 | Goldstein et al. | |
| 6,479,447 B2 | 11/2002 | Bijl et al. | |
| 6,501,000 B1 | 12/2002 | Stilbrany et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 7,524,444 B2 | 4/2009 | Hesse et al. | |
| 7,582,798 B2 | 9/2009 | Yaghi et al. | |
| 7,815,716 B2 | 10/2010 | Mueller et al. | |
| 2003/0004364 A1 | 1/2003 | Yaghi et al. | |
| 2003/0078311 A1 | 4/2003 | Muller et al. | |
| 2003/0148165 A1 | 8/2003 | Muller et al. | |
| 2003/0222023 A1 | 12/2003 | Mueller et al. | |
| 2004/0081611 A1 | 4/2004 | Muller et al. | |
| 2004/0225134 A1 | 11/2004 | Yaghi et al. | |
| 2004/0249189 A1 | 12/2004 | Mueller et al. | |
| 2004/0265670 A1 | 12/2004 | Muller et al. | |
| 2005/0004404 A1 | 1/2005 | Muller et al. | |
| 2005/0014371 A1 | 1/2005 | Tsapatsis | |
| 2005/0124819 A1 | 6/2005 | Yaghi et al. | |
| 2005/0154222 A1 | 7/2005 | Muller et al. | |
| 2005/0192175 A1 | 9/2005 | Yaghi et al. | |
| 2006/0057057 A1 | 3/2006 | Muller et al. | |
| 2006/0135824 A1 | 6/2006 | Mueller et al. | |
| 2006/0154807 A1 | 7/2006 | Yaghi et al. | |
| 2006/0185388 A1 | 8/2006 | Muller et al. | |
| 2006/0252641 A1 | 11/2006 | Yaghi et al. | |
| 2006/0252972 A1 | 11/2006 | Pilliod et al. | |
| 2006/0287190 A1 | 12/2006 | Eddaoudi et al. | |
| 2007/0068389 A1 | 3/2007 | Yaghi et al. | |
| 2007/0202038 A1 | 8/2007 | Yaghi et al. | |
| 2008/0017036 A1 | 1/2008 | Schultink et al. | |
| 2009/0155588 A1 | 6/2009 | Hesse et al. | |
| 2009/0247654 A1* | 10/2009 | Rajendran | C08J 9/0066 521/60 |

FOREIGN PATENT DOCUMENTS

| | | |
|---|---|---|
| WO | 2004101575 A2 | 11/2004 |
| WO | 2006072573 A2 | 7/2006 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A2 | 2/2009 |
| WO | 2009042802 A1 | 4/2009 |
| WO | 2009149381 A2 | 12/2009 |

OTHER PUBLICATIONS

Burrows et al., "Post-Synthetic Modification of Tagged Metal-Organic Frameworks." Angew. Chem. Int. Ed. (2008), 47, 8482-8486 (published online on Sep. 29, 2008).*

Kim, Su Mi, International Search Report and Written Opinion, Date of Mailing: Aug. 19, 2010, International Application No. PCT/US09/68731.

Nickitas-Etienne, Athina, International Preliminary Report on Patentability, Date of Mailing: Jun. 30, 2011, International Application No. PCT/US09/68731.

Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.

Carlucci, Lucia et al., "Polycatenation, polythreading and polyknotting in coordination network chemistry" Coordination Chemistry Reviews 246, 2003, pp. 247-289, Elsevier.

Chae et al., "Tertiary Building Units: Synthesis, Structure, and Porosity of a Metal-Organic Dendrimer Framework (MODF-1)," J. Am. Chem. Soc., 2001, 123, 11482-11483.

Chen et al., "Interwoven Metal-Organic Framework on a Periodic Minimal Surface with Extra-Large Pores," Science, 2001, 291, 1021-1023: Featured in Chemical and Engineering News, Feb. 21, 2001.

Chen et al., "Cu2(ATC) 6H2O: Design of Open Metal Sites in Porous Metal-Organic Crystals (ATC: 1,3,5,7-adamantane tetracarboxylate)," J. Am. Chem. Soc., 2000, 122, 11559-11560.

Han, SS et al., "Improved designs of metal-organic frameworks for hydrogen storage" Angew. Chem. Int. Ed. 2007, 46, pp. 6289-6292.

Howe, Patrick, International Search Report and Written Opinion, PCT/US2009/068849, European Patent Office, May 26, 2010.

Kim et al., "Assembly of Metal-Organic Frameworks from Large organic and Inorganic Secondary Building Units: New Examples and Simplifying Principles for Complex Structures," J. Am. Chem. Soc., 2001, 123, 8239-8247.

Kim, Su Mi, International Search Report and Written Opinion, Date of Mailing: Feb. 24, 2010, International Application No. PCT/US09/46463.

Li et al., "20 A [Cd4In16S35]14-Supertetrahedral T4 Clusters as Building Units in Decorated Cristobalite Frameworks,"J. Am. Chem. Soc., 2001, 123, 4867-4868.

Li et al., "Ge2ZrO6F2 (H2DAB)H2O: A 4-Connected Microporous Material with "Bow Tie" Building Units and an Exceptional Proportion of 3-Rings," J. Am. Chem. Soc., 2000, 122, 12409-12410.

Li et al., "Design and Synthesis of an Exceptionally Stable and Highly Porous Metal-Organic Framework," Nature, 1999, 402, 276-279: Featured in (1) Chemical and Engineering News, Nov. 22, 1999, and (2) Science News, Nov. 20, 1999.

Li et al., "Non-interpenetrating Indium Sulfide with a Supertetrahedral Cristobalite Framework," J. Am. Chem. Soc., 1999, 121, 6096-6097.

Li et al., "Supertetrahedral Sulfide Crystals with Giant Cavities and Channels," Science, 1999, 283, 1145-1147.

Li et al., "An Open-Framework Germanate with Polycubane-Like Topology," Angew. Chem. Int. Ed., 1999, 38, 653-655.

Li et al., "Transformation of Germanium Dioxide to 4-Connected Porous Germanate Net," J. Am. Chem. Soc., 1998, 120, 10569-10570.

Li et al., "Porous Germanates: Synthesis, Structure and Inclusion Properties of Ge7O14.5F2•[(CH3)2NH2]3(H2O) 0.86," J. Am. Chem. Soc., 1998, 120, 8567-8568.

Li et al., "Establishing Microporosity in Open Metal-Organic Frameworks: Gas Sorption Isotherms for Zn(BDC) (BDC=1,4-Benzenedicarboxylate)," J. Am. Chem. Soc., 1998, 120, 8571-8572.

Li et al., "Coordinatively Unsaturated Metal Centers in the Extended Porous Framework of Zn3(BDC)3•6CH3OH (BDC=1,4-Benzenedicarboxylate)," J. Am. Chem. Soc., 1998, 120, 2186-2187.

Loeb, SJ, "Rotaxanes as ligands: from molecules to materials" Chemical Society reviews, 2007, 36, pp. 226-235.

Morris et al., "Crystals as Moelcules: Postsynthesis Covalent Functionalization of Zeolitic Imidzolate Frameworks," J. Am. Chem Soc., 2008, 130(38):12626-12627, (Published on Web on Aug. 28, 2008).

Natarajan et al., "Non-crboxylate based metal-organic frameworks (MOFs) and related aspects," Curr. Opin. in Solid State and Mat. Science, 2009, vol. 13, pp. 46-53.

Nickitas-Etienne, Athina, International Preliminary Report on Patentability and Written Opinion, Date of Issuance of Report: Jan. 19, 2010, International Application No. PCT/US08/70149.

O'Keefe et al., "Frameworks for Extended Solids: Geometrical Design Principles," J. Solid State Chem., 2000, 152, 3-20.

O'Keefe et al., "Germanate Zeolites: Contrasting the Behavior of Germanate and Silicate Structures Built from Cubic T8O20 units (T=Si or Ge)," Chem. Eur. J., 1999, 5, 2796-2801.

Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.

(56) References Cited

OTHER PUBLICATIONS

Plevert et al.,"A Flexible Germanate Structure Containing 24-Ring Channels With Very Low Framework Density," J. Am. Chem. Soc., 2001, 123, 12706-12707.

Reineke et al., "Large Free Volume In Interpenetrating Networks: The Role of Secondary Building Units Exemplified by Tb2(ADB)3[(CH3)2SO]4•16[(CH3)2SO]," J. Am. Chem. Soc., 2000, 122, 4843-4844: Featured in Science Magazine, Editors Choice, Nov. 2000.

Reineke et al., "A Microporosity of Lanthanide-Organic Frameworks," Angew. Chem. Int. Ed., 1999, 38, 2590-2594.

Reineke et al., "From Condensed lanthanide Coordination Solids to Microporous Frameworks having Accessible Metal Sites," J. Am. Chem. Soc., 1999, 121, 1651-1657.

Rosi et al, "Infinite Secondary Building Units and Forbidden Catenation in Metal-Organic Frameworks," Angew. Chem. Int. Ed., 2002, 41, 294-297.

Rosi et al., "Advances in the Chemistry of Metal-Organic Frameworks," CrystEngComm, 2002, 4, 401-404.

Vodak et al., "Metal-Organic Frameworks Constructed from Pentagonal Antiprismatic and Cuboctahedral Secondary Building Units," Chem. Commun., 2001, 2534-2535.

Wang et al., "Tandem Modification of Metal-Organic Frameworks by a Postsynthetic Approach," Angew. Chem. Int. Ed. 2008, 47, pp. 4699-4702.

Wang et al., "Postsynthetic Covalent Modification of a Neutral Metal-Organic Framework," J. Am Chem. Soc., 2007, 129(41), 12368-12369.

Wong-Foy, AG et al., "Exceptional H2 saturation uptake in microporous metal-organic frameworks" J. Am. Chem. Soc., 2006, 128, pp. 3494-3495.

Yaghi et al., "Synthetic Strategies, Structure Patterns, and Emerging Properties in the Chemistry of Modular Porous Solids," Acc. Chem. Res., 1998, 31, 474-484.

Yaghi et al., "Construction of a New Open-Framework Solid from 1,3,5-Cyclohexanetricarboxylate and Zinc(II) Building Blocks," J. Chem. Soc., Dalton Trans., 1997, 2383-2384.

Yaghi et al., "A Molecular Railroad with Large Pores: Synthesis and Structure of Ni(4,4'-bpy)2.5(H2O)2(ClO4)2•1.5 (4,4'-bpy)2(H2O)," Inorg. Chem., 1997, 36, 4292-4293.

Yaghi et al., "Crystal Growth of Extended Solids by Nonaqueous Gel Diffusion," Chem. Mater., 1997, 9, 1074-1076.

Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.

Yaghi et al., "Construction of Porous Solids from Hydrogen-Bonded Metal Complexes of 1,3,5-Benzenetricarboxylic Acid," J. Am. Chem. Soc., 1996, 118, 9096-9101.

Yaghi et al., "T-Shaped Molecular Building Units in the Porous Structure of Ag(4,4'-bpy) NO3," J. Am. Chem. Soc., 1996, 118, 295-296.

Yaghi et al., "Hydrothermal Synthesis of a Metal-Organic Framework Containing Large Rectangular Channels," J. Am. Chem. Soc., 1995, 117, 10401-10402.

Yaghi et al., "Open-Framework Solids with Diamond-Like Structures Prepared from Clusters and Metal-Organic Building Blocks,"Mater. Res. Soc. Symp. Proc., 1995, 371, 15.

Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.

Yaghi et al., "Presence of Mutually Interpenetrating Sheets and Channels in the Extended Structure of Cu(4,4'-Bipyridine)Cl," Angew. Chem. Int. Ed. Engl., 1995, 34, 207-209.

Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.

Yaghi et al., "Selective binding and removal of guests in a microporous metal-organic framework," Nature, Dec. 1995, pp. 703-706, vol. 378.

Young, Lee W., International Search Report and Written Opinion, Date of Mailing: Jan. 12, 2009, International Application No. PCT/US08/70149.

* cited by examiner

POROUS REACTIVE FRAMEWORK

CROSS REFERENCE TO RELATED APPLICATIONS

This application is a U.S. National Stage Application filed under 35 U.S.C. §371 based upon International Application No. PCT/US09/68731, filed Dec. 18, 2009, which application claims priority under 35 U.S.C. §119 to U.S. Provisional Application Ser. No. 61/138,732, filed Dec. 18, 2008, the disclosures of which are incorporated herein by reference in its entirety.

STATEMENT REGARDING FEDERALLY SPONSORED RESEARCH

The invention was made with Government support of Grant No. W911NF-06-1-0405 awarded by the United States Army, Joint Science and Technology Office. The government has certain rights in the invention.

FIELD OF THE INVENTION

This disclosure relates to porous frameworks for gas separation, sensing and drug/biomolecule delivery. More particularly, the disclosure relates to reactive porous frameworks for functionalization.

BACKGROUND

The ability to functionalize molecules is a long standing practice in organic chemistry that has led to advances in the synthesis of natural products, pharmaceuticals, and polymers. However, the analogous chemistry of crystalline extended solids remains undeveloped because they generally lose their structural integrity under the reaction conditions required to carry out meaningful organic transformations.

SUMMARY

The disclosure provides a method of generating post-reactive framework (PRF) comprising: generating a porous framework comprising a metal organic framework (MOF), a zeolitic framework, a zeolitic imidazole framework (ZIF), a covalent organic framework (COF) or a biocompatible organic framework (BOF), wherein a linking moiety of the porous framework comprises one or more reactive side groups selected from the group consisting of —NH$_2$, —CN, —OH, =O, =S, —SH, —P, —Br, —CL, —I, —F,

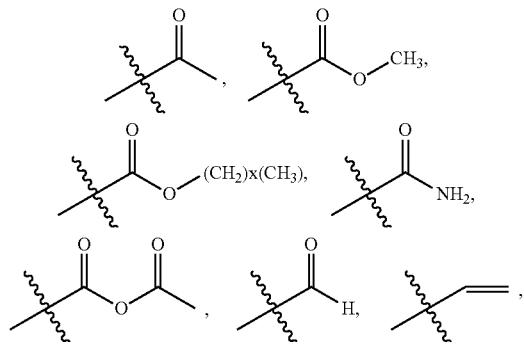

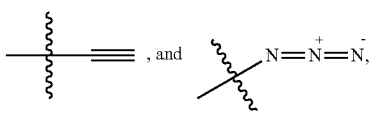

wherein X=1, 2, or 3; and reacting the framework with a post framework reactant comprising an organic species under conditions wherein the post framework reactant modifies the reactive side group to form a PRF. In one embodiment, the porous framework comprises a general structure M-L-M, wherein the M is transition metal and L is a linking moiety. In another embodiment, the L comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings and a linking cluster covalently bound to the substructure. In yet another embodiment, the linking moiety substructure is selected from any of the following:

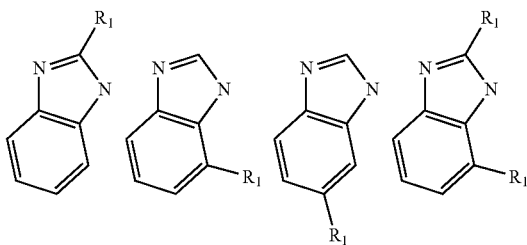

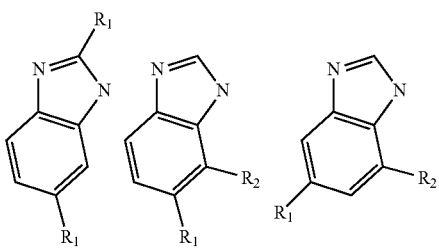

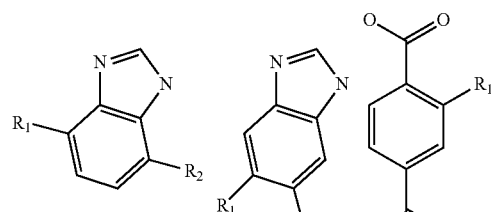

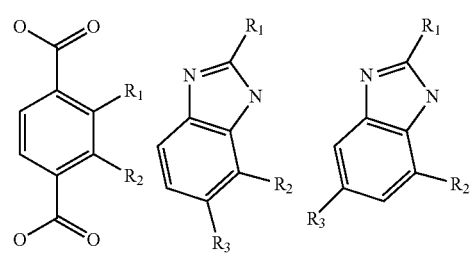

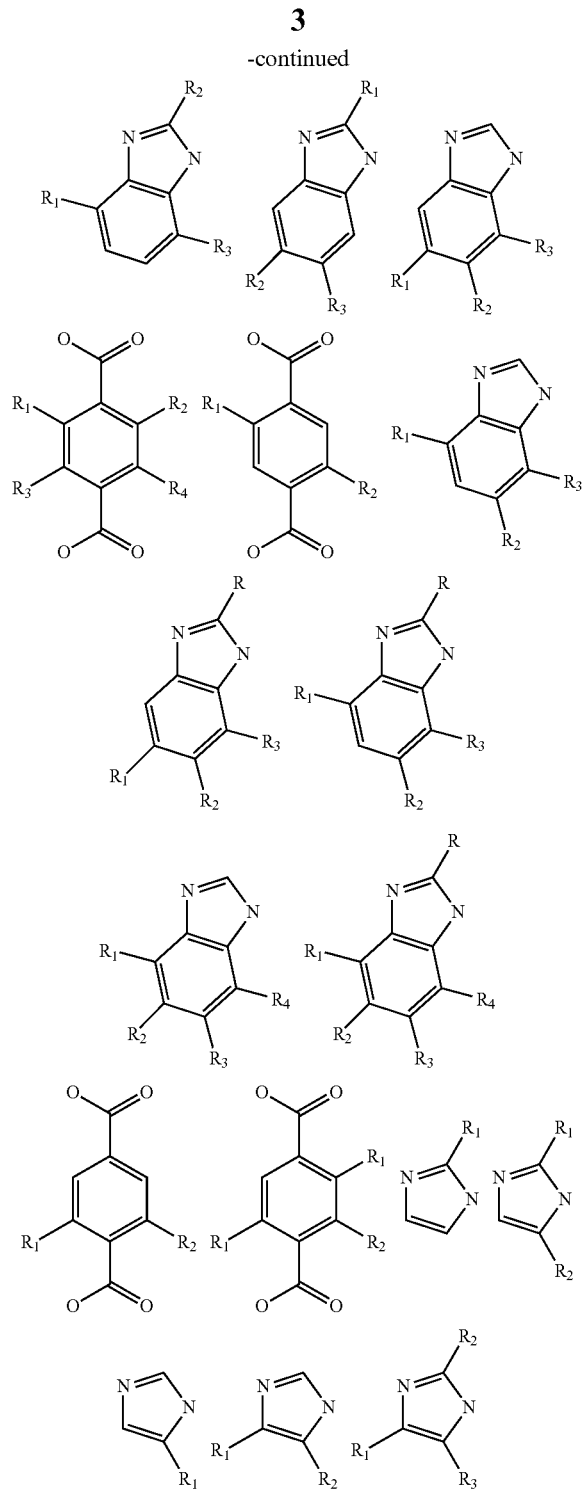

wherein R1, R2, R3, R4 are each individually selected from the group consisting of —NH$_2$, —CN, —OH, =O, =S, —SH, —P, —Br, —Cl, —I, —F,

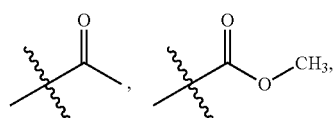

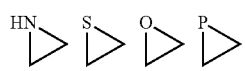

wherein X=1, 2, or 3. In yet another embodiment, the post framework reactant comprises a ring structure of 1-20 carbons with functional groups comprising atoms such as N, S, O, and P. In one embodiment, a metal and metal containing compounds that chelate to and add functional groups to the reactive side group is used. In another embodiment, the post framework reactant undergoes reaction with the porous framework that result in the tethering of organometallic complexes to the framework. In yet another embodiment, the post framework reactants comprises a heterocyclic compound. In one embodiment, the heterocyclic compound has one or more multivalent heteroatoms, independently selected from N, O and S, as a part of the ring structure. In yet another embodiment, the heterocylic compound comprises a monocyclic heterocycle. In yet a further embodiment, the monocyclic heterocycle is selected from the group consisting of: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. In yet an even further embodiment, the heterocycle is selected from the group consisting of:

In one embodiment, the reaction is carried out under mild conditions with reagents that result in a modification of a reactive side group that fits with the pore size of the porous framework. In one embodiment, the post reactive framework comprises a modification of the linker moiety comprising an aliphatic sulfonic acid group. In some embodiments, a guest species is removed from the porous framework prior to reacting the framework with the post framework reactant. In another embodiment, the disclosure provides a method of generating a post-reactive (PRF) framework comprising generating a porous framework comprising a ZIF, a COF, a MOF or a BOF wherein a linking moiety of the porous framework comprises one or more reactive side groups selected from the group consisting of secondary or tertiary amine, CN, OH, =O, =S, SH, P, Br, CL, I, F,

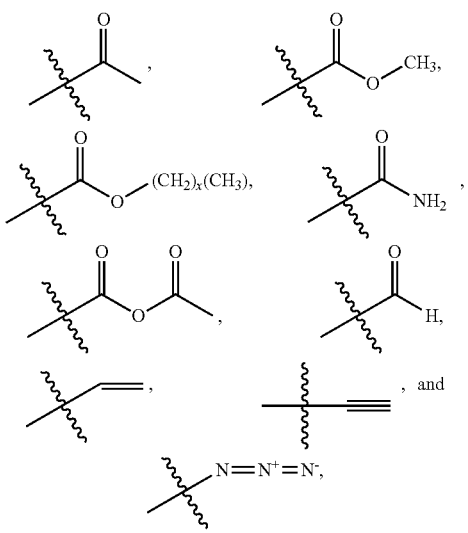

wherein X=1, 2, or 3; and reacting the framework with a post framework reactant comprising an organic species under conditions wherein the post framework reactant adds to the reactive side group and then the reactive side group is eliminated to form a PRF.

The disclosure also provides post reactive frameworks PRFs produced by the methods above. In yet another embodiment, the PRFs are used in gas sorption, sensing, filtration and in catalysis.

The disclosure also provides a porous framework comprising a plurality of multidentate cores linked to one another by a linking moiety, the linking moiety comprising a side group selected from the group consisting of $NH_2$, CN, OH, =O, =S, SH, P, Br, CL, I, F,

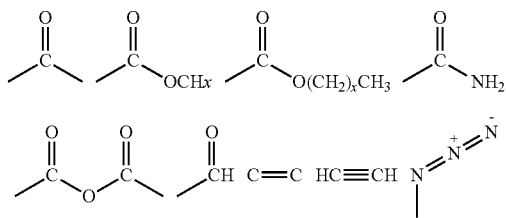

wherein X=1, 2, or 3 in addition to a linking cluster.

The disclosure provides methods to generate reactive species in porous organic frameworks and compositions derived there from. The methods and compositions extend to metal organic frameworks (MOFs), covalent organic frameworks (COFs), zeolitic imidazolate frameworks (ZIFs) and biocompatible organic frameworks (BOFs). The porous reactive frameworks of the disclosure have unusual thermal and chemical stability and thus are ideal platforms for performing useful organic transformations under strong reaction conditions. For example, the imidazolate-2-carboxaldehyde (ICA) links, which join tetrahedral zinc(II) centers in a porous ZIF, were reduced by $NaBH_4$ to the corresponding alcohol derivative, and converted to an imine functionality in refluxing methanol. Despite these strong reaction conditions, the integrity of the structure and its crystallinity are maintained throughout the synthesis. The isolated ZIF derivatives indicate that those organic reactions proceeded in high conversions. In essence the success in achieving typical organic reactions in crystals of extended structures like ZIFs makes the idea of using the "crystal as a molecule" a reality and opens many opportunities for employing the arsenal of organic reactions in the covalent functionalization of extended structures.

The disclosure provides both methods for modifying a framework after crystallization as well as compositions comprising such post-reactive frameworks. ZIFs-91 and -92 are exemplar of the disclosure, being MOFs that were synthesized after the framework had been crystallized. Other MOFs that fall into this category are IRMOF-3n and IRMOF-3s as well as Zr-MOF-1n. These MOFs are based on classical amine-containing structures, but are reacted with 2-methylaziridine (in the -n cases) or 1,3-propanesultone (in the -s case). Using such methods of post crystallization one can generate a multitude of frameworks having tuned pores. In one embodiment, MOFs comprising a 2,2'-bipyridine unit in the framework, to which can be bound a wide variety of metal ions (e.g., Pt) can be generated. All of these frameworks maintain porosity after reaction with the exception of ZIF-92, which has substantially filled pores after modification.

DETAILED DESCRIPTION

Figure 1:
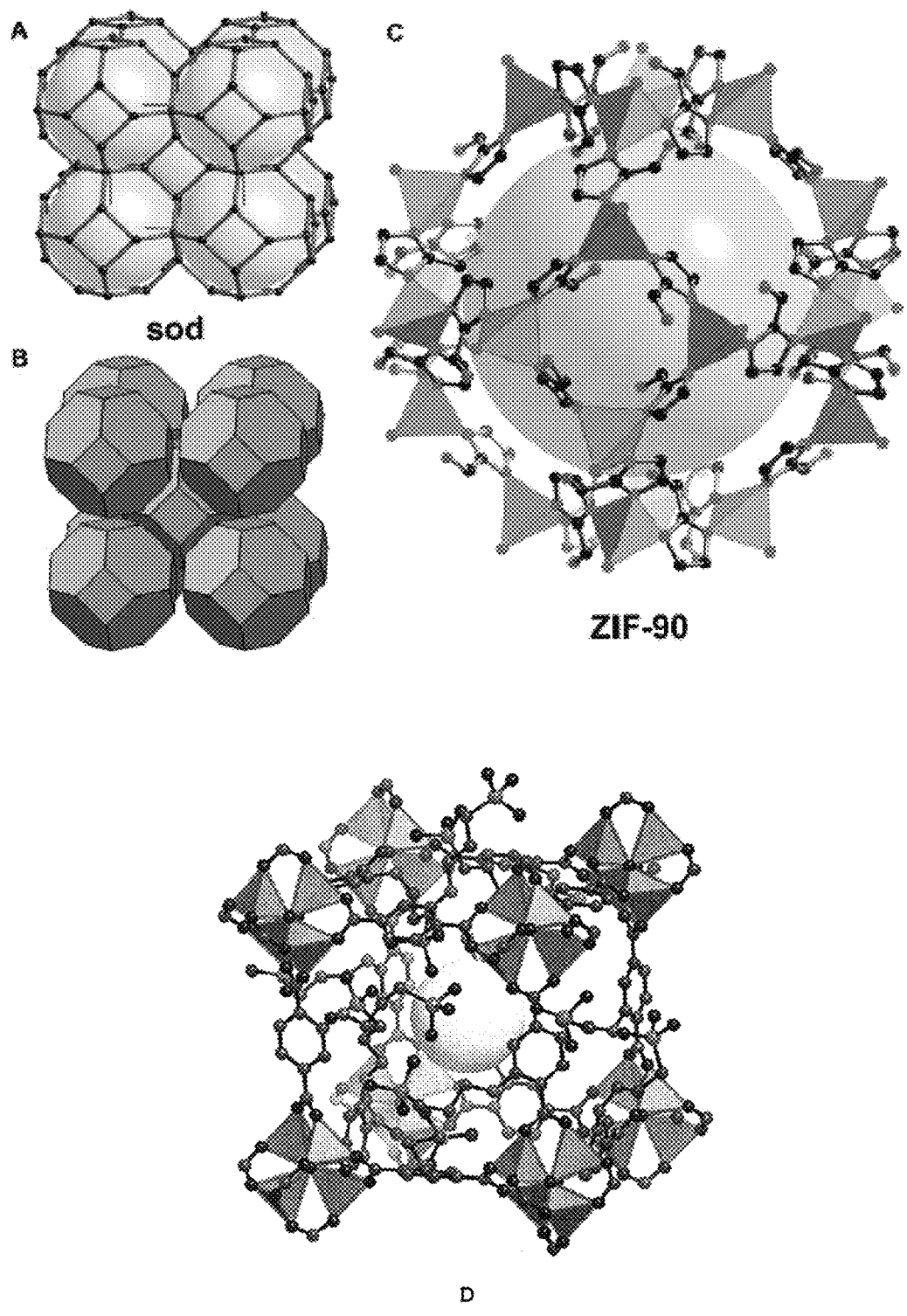
FIG. 1A-D shows a crystal structure of ZIF-90 presented as (A) a net (line and black dot drawing), (B) a tiling to show the subdivision of space (polyhedra) in the sodalite topology, and (C) a cut away view of one of the ZIF cages with $ZnN_4$ tetrahedra polyhedra and the ICA links in ball-and-stick representation (C, black; N, light gray; O, dark gray). The ball represents the largest sphere to fit in the porous cage without contacting the van der Waals spheres of the framework. H atoms have been omitted for clarity. (D) a sulfonated IRMOF-3 comprising a aliphatic sulfonic acid group linked to a linking moiety of the underlying framework.

As used herein and in the appended claims, the singular forms "a," "and," and "the" include plural referents unless the context clearly dictates otherwise. Thus, for example, reference to "a species" includes a plurality of such species and reference to "the framework" includes reference to one or more frameworks and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The disclosure demonstrates the functionalizing of organic links of porous metal-organic frameworks post-synthesis using, for example, mild organic reactions. Such porous reactive frameworks (PRFs) include metal organic frameworks (MOFs), zeolitic-imidazolate frameworks (ZIFs), covalent-organic frameworks (COFs) and biocompatible organic frameworks (BOFs) that result in materials with useful pore functionalities that cannot be accessed by traditional synthetic methods (i.e., by inclusion on the organic linker prior to framework synthesis). The methods are also cheaper or more expedient than traditional synthetic methods. The PRFs of the disclosure are suitable for, e.g., catalysis, gas separation, gas storage, sensing, ion conduction, ion exchange membranes and drug delivery. Organic frameworks of the disclosure have the general structure M-L-M, wherein L is a linking moiety and M are transition metals or polydentate core. The disclosure takes advantage of the modification of exposed side group on a linking moiety, post synthesis, that can be reactive and functionalized by a post-framework reactant under suitable reaction conditions.

As used herein, a "core" refers to a repeating unit or units found in a framework. Such a framework can comprise a homogenous repeating core or a heterogeneous repeating core structure. A core comprises a transition metal or cluster of transitions metals that can be linked to a linking moiety. A plurality of cores linked together through a linking group defines a framework.

The term "cluster" refers to identifiable associations of 2 or more atoms. Such associations are typically established by some type of bond—ionic, covalent, Van der Waal, and the like.

A "linking cluster" refers to a one or more reactive species capable of condensation comprising an atom capable of forming a bond between a linking moiety substructure and a metal group or core, or between a linking moiety and another linking moiety. Examples of such species are selected from the group consisting of a boron, oxygen, carbon, nitrogen, and phosphorous atom. In some embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2/C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, CH(OH)$_2$, C(OH)$_3$, CH(CN)$_2$, and C(CN)$_3$, wherein R is an alkyl group having from 1 to 5 carbon atoms, or an aryl group comprising 1 to 2 pheny rings.

The term "covalent organic polyhedra" refers to a non-extended covalent organic network. Polymerization in such polyhedra does not occur usually because of the presence of capping ligands that inhibit polymerization. Covalent organic polyhedra are covalent organic networks that comprise a plurality of linking clusters linking together multi-dentate cores such that the spatial structure of the network is a polyhedron. Typically, the polyhedra of this variation are 2 or 3 dimensional structures.

A "linking moiety" refers to a mono-dentate or polydentate compound that bind a transition metal or a plurality of transition metals or cores, respectively. Generally a linking moiety comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which a linking cluster (e.g., a multidentate function groups) are covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically the linking moiety will comprise a substructure having one or more carboxylic acid linking clusters covalently attached.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In one embodiment, the linking moiety is selected from any of the following:

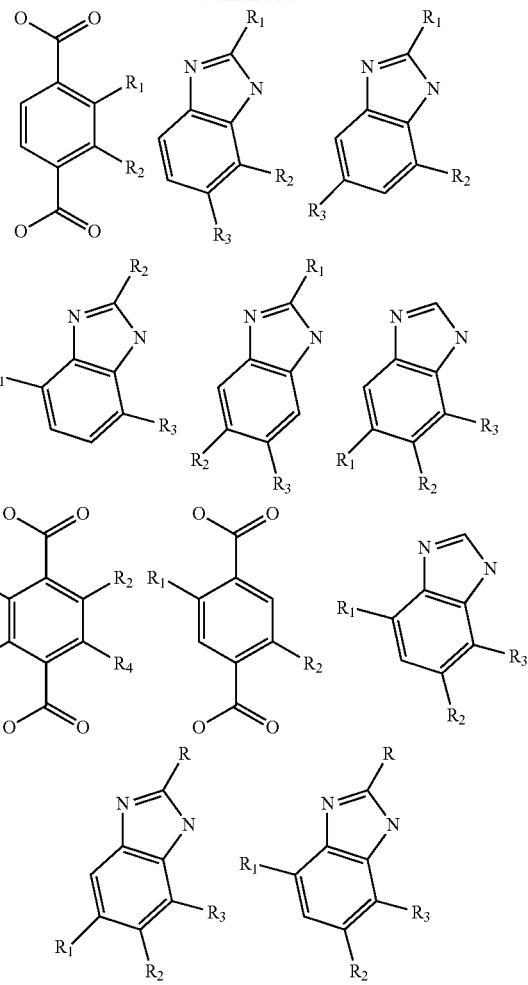

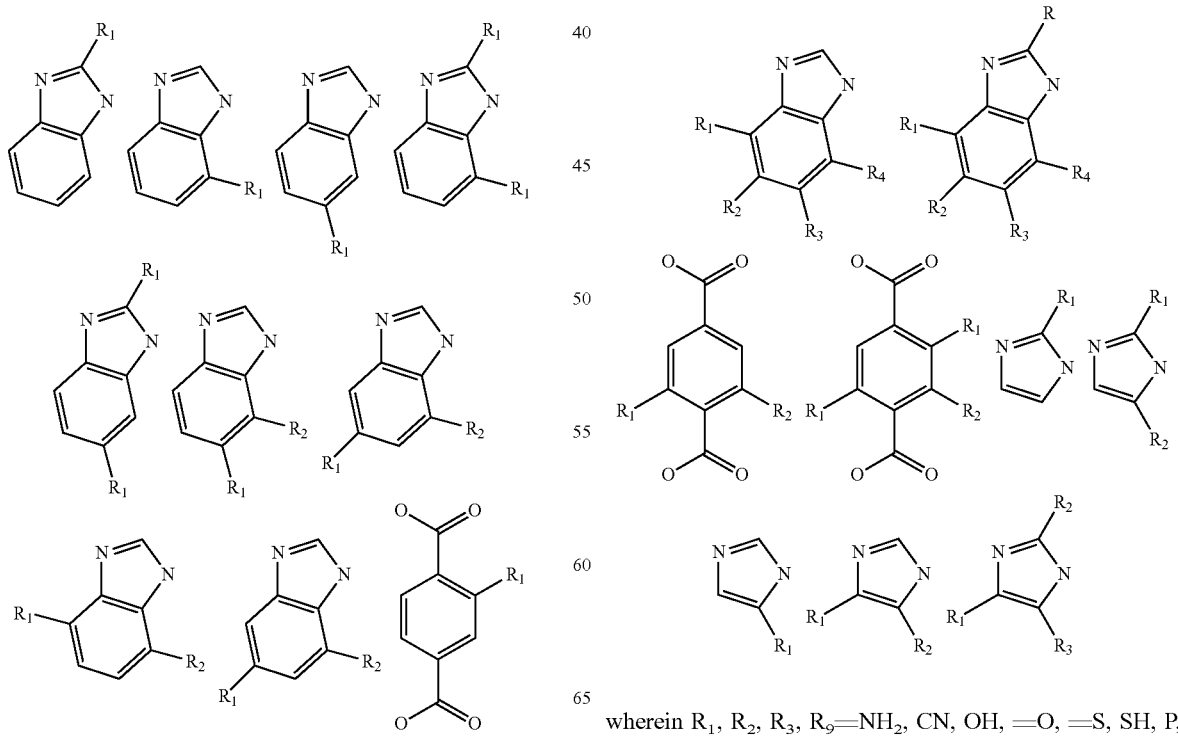

wherein R$_1$, R$_2$, R$_3$, R$_9$=NH$_2$, CN, OH, =O, =S, SH, P, Br, CL, I, F,

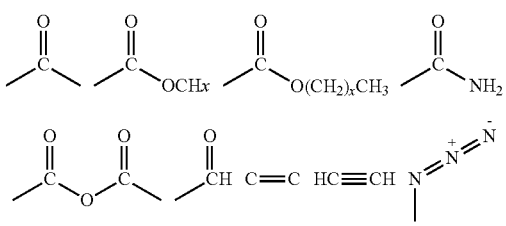

wherein X=1, 2, or 3. Further examples of ZIFs, MOFs, COFs and BOFs comprising linking moieties are set forth herein.

A post framework reactant refers to any organic reactant. Rings of 1-20 carbons with functional groups comprising atoms such as N, S, O, and P are useful. In addition, metal and metal containing compounds that may chelate to and add functional groups or a combination of previously existing and newly added functional groups are also useful. Reactions that result in the tethering of organometallic complexes to the framework for use as, for example, a heterogeneous catalyst can be used. For example, converting a reactive side group in a linking agent to an alcohol followed by reacting the group with an alkali earth metal to generate a metal alkoxide is provided.

Examples of post framework reactants include, but are not limited to, heterocyclic compounds. In one embodiment, the post framework reactant can be a saturated or unsaturated heterocycle. The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms there between. Heterocycle may have aromatic character or may not have aromatic character. The terms "heterocyclic group", "heterocyclic moiety", "heterocyclic", or "heterocyclo" used alone or as a suffix or prefix, refers to a radical derived from a heterocycle by removing one or more hydrogens there from. The term "heterocyclyl" used alone or as a suffix or prefix, refers a monovalent radical derived from a heterocycle by removing one hydrogen there from. The term "heteroaryl" used alone or as a suffix or prefix, refers to a heterocyclyl having aromatic character. Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydropyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. For example, heterocycles useful in the methods of the disclosure include:

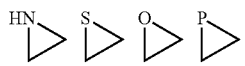

In addition, heterocycle includes aromatic heterocycles (heteroaryl groups), for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

In the methods of the disclosure a post reactive framework agent is contacted with a ZIF, MOF, COF, or BOF framework to functionally modify the framework including pore size, binding capacity (e.g., free reactive side groups, charge etc). Accordingly, the ZIF, MOF, COF or BOF frameworks can be modified for a desired purpose or use by selecting a post reactive framework agent to generate the desired porosity, charge and the like.

A "zeolitic framework," as used herein, refers to a framework of repeating cores having a zeolite-type structure. A zeolitic framework can comprise a structure as set forth in the Atlas of Zeolite Structure Types.

A "zeolitic imidizolate framework" or "ZIF" refers to a zeolitic framework comprising a zeolitic structure having an imidizole, imidizolate-derivative, or imidizolate linking moiety.

A zeolitic frameworks can comprise a network of homogenous transition metal or heterogeneous transition metals linked by a homogenous or heterogeneous linking moiety. The zeolitic frameworks of the disclosure can comprise any of the networks currently defined in the Atlas of Zeolite Structure Types known in the literature as well as POZ. The zeolitic frameworks of the disclosure provide nanoporous structure useful for filtration, gas storage and the like, as more fully described herein. Using the methods of the disclosure the ZIFs can be modified post synthesis using a post reactive agent of the disclosure to change or modify the porosity or charge of the framework.

The disclosure also provide a general synthesis of structures having zeolite framework topologies in which all tetrahedral atoms are transition metals, and the linking moieties comprise organic linkers comprising nitrogen, sulfur or oxygen organic molecules (e.g., such as imidazolate (IM) units). The organic linkers may be further functionalized to modify the cage size and pore size or specificity to a guest species or gas molecule.

Zeolitic frameworks comprise the general structure M-L-M, wherein M comprises a transition metal and L is a linking moiety. In one embodiment, the framework comprising and M-L-M structure is selected from the group consisting of:

(a) M-L-M, wherein L comprises structure III; and
(b) M-L-M, wherein at least one L is structure III and at least one other L is a structure I, II or a combination thereof:

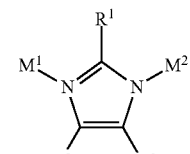

(I)

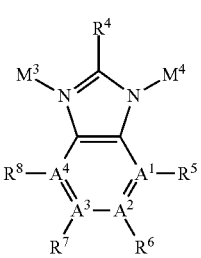

(II)

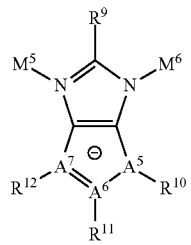

(III)

wherein A can be either C or N, wherein $R^5$-$R^9$ are present when $A^1$ and $A^4$ comprise C, wherein $R^1$, $R^4$ or $R^9$ comprise a non-sterically hindering group that does not interfere with M, wherein $R^2$, $R^3$, $R^5$, $R^8$, $R^{10}$, $R^{11}$, $R^{12}$ are each individually an alkyl, halo-cyano-nitro-, wherein when the linking moiety comprises structure III, $R^{10}$, $R^{11}$ and $R^{12}$ are each individually electron withdrawing groups, and wherein one of $R^6$ and $R^7$ comprise an electron withdrawing group.

In one embodiment, $R^1$, $R^4$ or $R^9$ comprise a non-sterically hindering electron donating group that does not interfere with M. The $R^1$, $R^4$ or $R^9$ functionalized with a group selected to interact with a particular gas or substrate. In another embodiment, $R^2$, $R^3$, $R^6$, $R^7$, or $R^{11}$ are individually H or a small electron withdrawing group. In one aspect, the small electron withdrawing group is of sufficient size to increase a cage size for a ZIF of the disclosure. For example, $R^7$ can be a chloro-group.

In a further embodiment the imidazolate or imidazolate derivative is selected from the group consisting of IV, V, VI, VII, VIII, and IX:

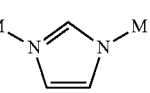

IV

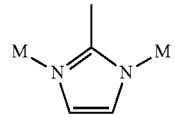

V

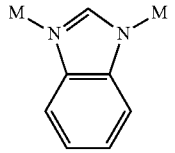

VI

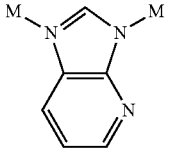

VII

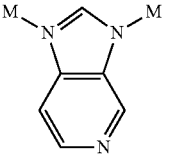

VIII

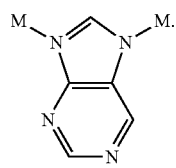

IX

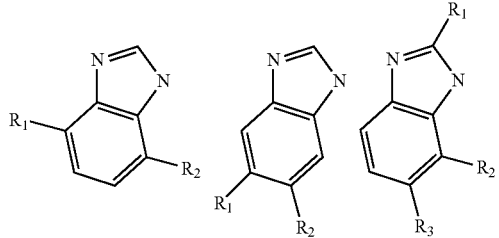

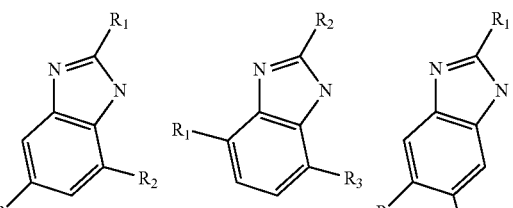

In one embodiment, the imidazolate or imidazolate derivative is selected from the group consisting of a substituted imidazolate; a benzimidazolate comprising a methyl-, nitro-, cyano, or chloro-group; an azabenzimidazolate; and an azabenzimidazolate wherein one or two carbon atoms on the benzimidazolate are replaced by nitrogen. The transition metal is selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one aspect, a zeolitic framework comprises a heterogeneous combination of transition metals. In yet another embodiment, the zeolitic framework comprises homogenous transition metal but a heterogeneous combination of linking moieties. In a further embodiment, a zeolitic framework comprises a heterogeneous mixture of transition metals and linking moieties.

In yet another embodiment, the linking moiety comprises a benzimidazolate (bIM) functionalized at the 5 or 4 and 5 positions to modify the pore character and/or cage structure of the framework. The functionalization moiety is used to increase the IM girth and comprises a small electron withdrawing group. The functionalization moiety can comprise, for example, a chloro-, bromo-, iodo- or fluoro-containing group. For example, the disclosure provides a 5-chlorobenzimidazolate (cbIM) linked to a transition metal selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one aspect, the cbIM linking moiety is linked to a Zn or Co transition metal.

In one embodiment, the imidazolate or imadazolate derivative linking moiety (metal groups not depicted) has a structure selected from the group consisting of:

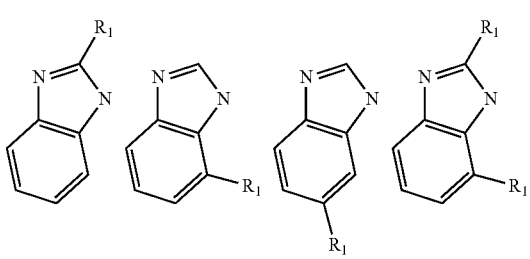

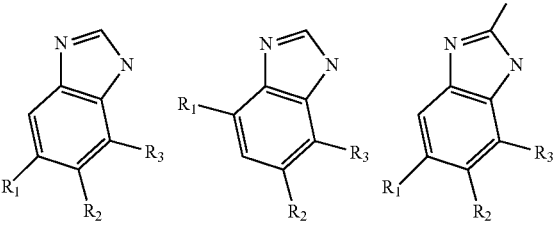

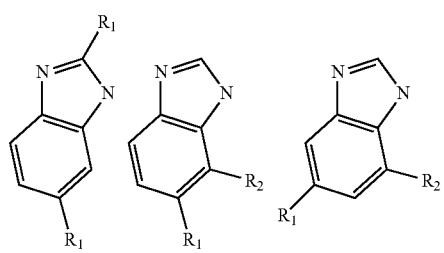

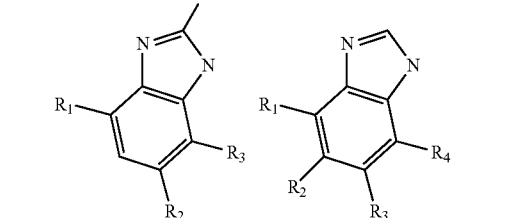

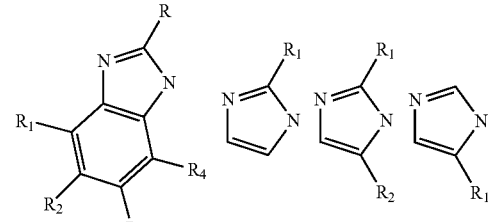

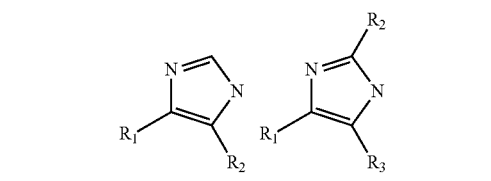

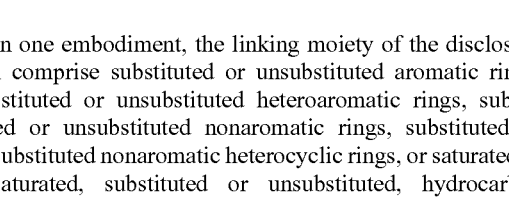

In one embodiment, the linking moiety of the disclosure can comprise substituted or unsubstituted aromatic rings, substituted or unsubstituted heteroaromatic rings, substituted or unsubstituted nonaromatic rings, substituted or unsubstituted nonaromatic heterocyclic rings, or saturated or unsaturated, substituted or unsubstituted, hydrocarbon groups. The saturated or unsaturated hydrocarbon groups may include one or more heteroatoms. For example, the linking moiety substructure can comprise Formula XI:

(XI)

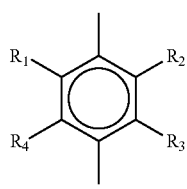

wherein $R_1$, $R_2$, $R_3$, and $R_4$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters.

In one embodiment, the linking group comprises a structure selected from the group consisting of:

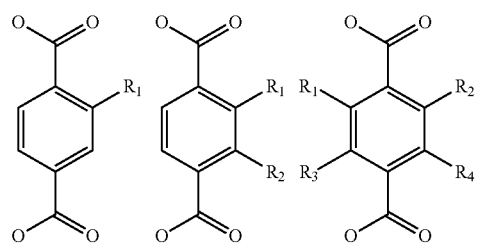

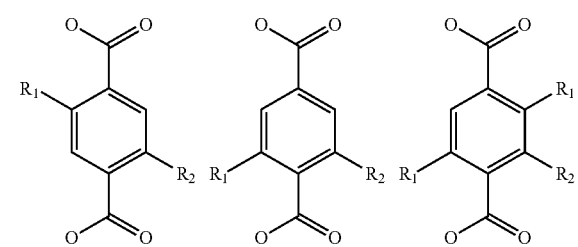

wherein the carboxylic acid groups above undergo a condensation with a transition metal to form a framework and wherein $R_1$, $R_2$, $R_3$, $R_4$=$NH_2$, CN, OH, =O, =S, SH, P, Br, CL, I, F,

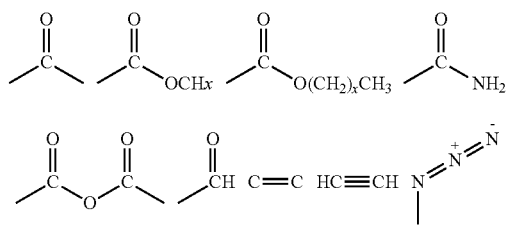

wherein X=1, 2, or 3.

In another variation of the linking moiety is described by Formula XII:

(XII)

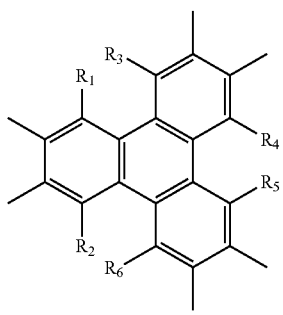

wherein $R_1$, $R_2$, $R_3$, $R_4$, $R_5$, and $R_6$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one aspect, $R_1$, $R_2$, $R_3$, $R_4$ are each independently selected from the group consisting of $NH_2$, CN, OH, =O, =S, SH, P, Br, CL, I, F,

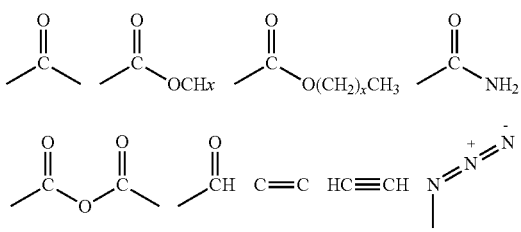

wherein X=1, 2, or 3.

In another variation the linking moiety is described by Formula XIII-XVI:

(XIII)

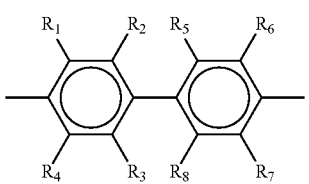

(XIV)

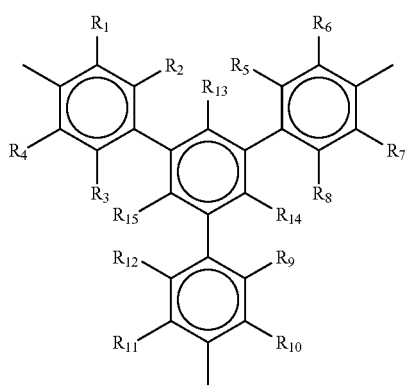

-continued

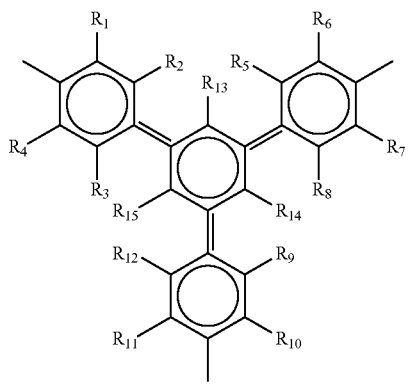
(XV)

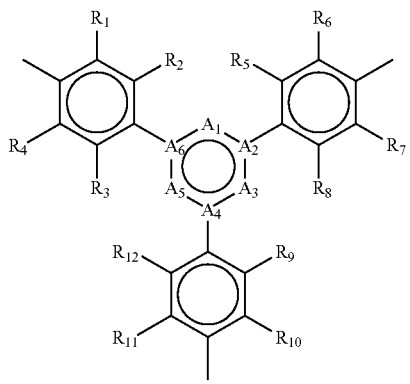
(XVII)

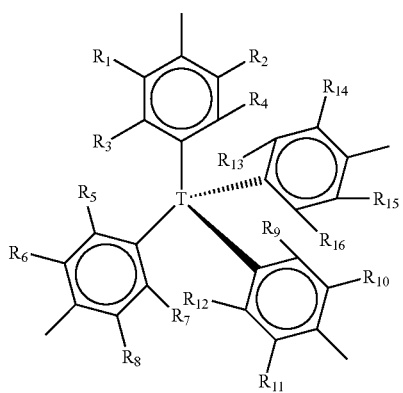
(XVI)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters and T is a tetrahedral atom (e.g., carbon, silicon, germanium, tin) or a tetrahedral group or cluster. In one aspect, $R_1$, $R_2$, $R_3$, $R_4$ are each independently selected from the group consisting of $NH_2$, CN, OH, =O, =S, SH, P, Br, CL, I, F,

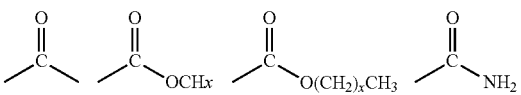

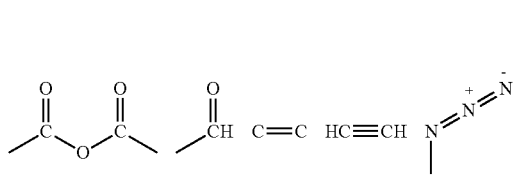

wherein X=1, 2, or 3.

In another variation the linking moiety is described by Formula XVII:

wherein $A_1$, $A_2$, $A_3$, $A_4$, $A_5$, and $A_6$ are each independently absent or any atom or group capable of forming a sable ring structure and $R_1$, $R_2$, $R_3$, $R_4$, $R_5$, $R_6$, $R_7$, $R_8$, $R_9$, $R_{10}$, $R_{11}$, and $R_{12}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one aspect, $R_1$, $R_2$, $R_3$, $R_4$ are each independently selected from the group consisting of $NH_2$, CN, OH, =O, =S, SH, P, Br, CL, I, F, wherein X=1, 2, or 3. Specific examples of Formula XVII are provided by Formulae XVIII and XIX and ammonium salts of the linking groups of Formulae XVIII and XIX:

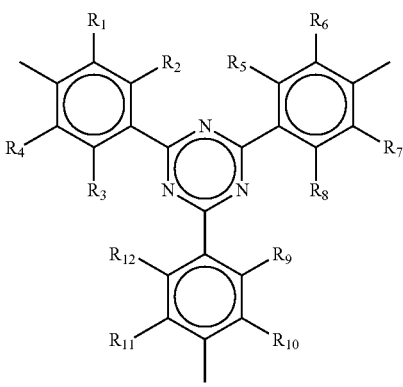
(XVIII)

-continued

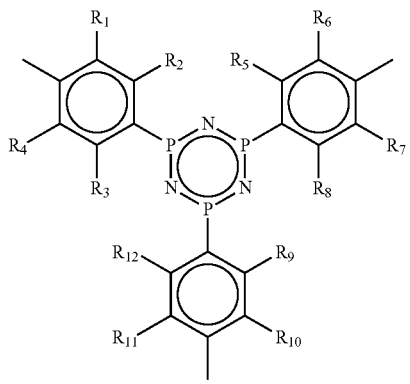

(XIX)

wherein $R_1$, $R_2$, $R_3$, $R_4$, $R_5$, $R_6$, $R_7$, $R_8$, $R_9$, $R_{10}$, $R_{11}$, and $R_{12}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one aspect, $R_1$, $R_2$, $R_3$, $R_4$ are each independently selected from the group consisting of $NH_2$, CN, OH, =O, =S, SH, P, Br, CL, I, F,

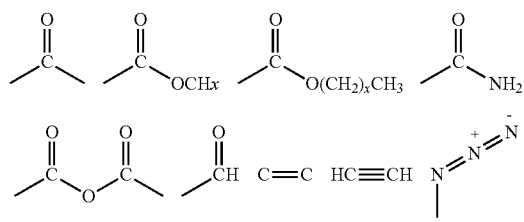

wherein X=1, 2, or 3.

In yet another variation the linking moiety is described by Formula XX:

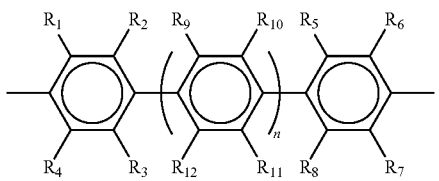

(XX)

wherein $R_1$ through $R_{12}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters; and n is an integer greater than or equal to 1. In one aspect, $R_1$, $R_2$, $R_3$, $R_4$ are each independently selected from the group consisting of $NH_2$, CN, OH, =O, =S, SH, P, Br, CL, I, F,

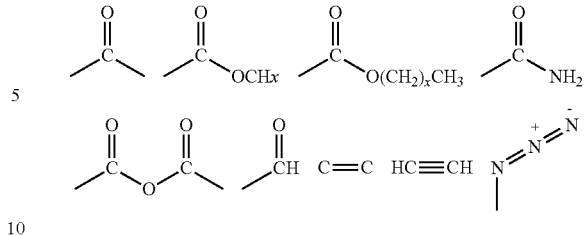

wherein X=1, 2, or 3.

A framework can undergo post synthetic modification by reacting the framework with a reactive specie. For example, if $R_2$ of Formula XI is $NH_2$ reaction with an aziridine containing compound results in opening of the reactive species ring depicted generally by:

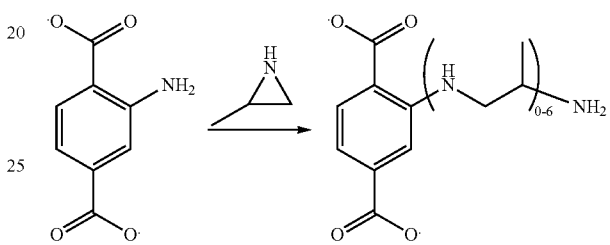

Using such methods variations and functionalized frameworks can be generated. As shown above, the reaction of the linking moiety with a aziridine results in the addition of a side group to the linking moiety. In such a framework the reactive side group can extend into the pores of the framework thereby modifying their size or charge.

The disclosure provides post synthesis functionalized frameworks (PRFs). PRFs comprise the general structure M-L-M wherein the transition metals or cores are linked by a linking moiety that comprises a side group useful for post synthesis modification.

The PRFs can comprise any of the types assigned by X-ray analysis to the ABW, AGO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG and ZON structure and to mixed structures of two or more of the above mentioned structures.

Useful transition metal comprise any one or more of the following: Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub. In a specific embodiment, the transition metal is Zn or Co.

The framework (e.g., a PRF) of the disclosure can take any framework/structure. For example, using the methods of the disclosure, ZIFs having any of the following framework codes can be obtained: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, ISV, ITE, ITH, ITW, IWR, IWV, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, and ZON.

A framework of the disclosure, such as a ZIF, can be synthesized by using solvothermal methods. Highly crystalline materials are obtained by combining the requisite hydrated metal salt (e.g., nitrate) and, for example, an imidazole-type linker in an amide solvent such as N,N-diethylformamide (DEF). The resulting solutions are heated (85-150° C.) and zeolitic frameworks of the disclosure are precipitated after 48-96 h and were readily isolated.

The disclosure also provides covalently linked organic frameworks (COFs). Typically in a COF each linking moiety is linked to at least one, typically two, distinct linking moieties. In a further refinement these COFs are crystalline materials that may be either polycrystalline or even single crystals. The linking moiety may be the same throughout the net (i.e., a homogenous net) or may be different or alternating types of multidentate cores (i.e., a heterogeneous net; in this aspect the denticity refers to the number of neighboring cores to which a particular core is bound). Since the covalently bonded organic frameworks are extended structures, variation may form into analogous nets to the nets found in metallic organic frameworks as described in Reticular Chemistry: Occurrence and Taxonomy of Nets and Grammar for the Design of Frameworks, Acc. Chem. Res. 2005, 38, 176-182. The entire disclosure of this article is hereby incorporated by reference.

The disclosure provides a covalent organic framework comprising two or more organic linking moieties covalently bonded to a linking cluster, the linking cluster comprising an identifiable association of 2 or more atoms, wherein the covalent bonds between each linking moiety and the linking cluster take place between atoms selected from carbon, boron, oxygen, nitrogen and phosphorus and at least one of the atoms in each covalent bond between a linking moiety and the linking cluster is oxygen. One or more COFs can be covalently bonded to one another each COF can be identical or different in structure.

The covalently linked organic frameworks or polyhedra of the disclosure optionally further comprise a guest species. Such a guest species may increase the surface area of the covalently linked organic networks. In a similar manner, the covalently linked organic networks of the disclosure further comprise an adsorbed chemical species. Such adsorbed chemical species include for example, ammonia, carbon dioxide, carbon monoxide, hydrogen, amines, methane, oxygen, argon, nitrogen, organic dyes, polycyclic organic molecules, metal ions, inorganic clusters, organometallic clusters, and combinations thereof. In one aspect, the linking moiety further comprises a side group selected from the group consisting of $NH_2$, CN, OH, =O, =S, SH, P, Br, CL, I, F,

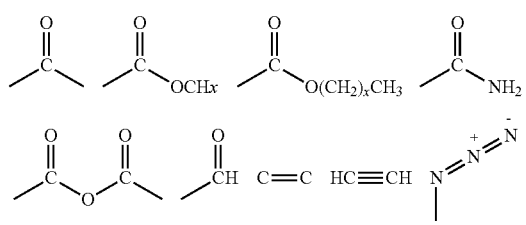

wherein X=1, 2, or 3 in addition to the linking cluster. Such side groups are useful for post-synthetic modification of the COF framework using reactive species such as a heterocycle as described above.

A method for forming a covalently linked organic frameworks and polyhedra set forth above is provided. In one variation of this embodiment, the method utilizes a linking moiety comprising at least one boron-containing cluster for use in condensation into an extended crystalline materials. Such linking moiety comprises a boron-containing cluster that self-condenses with other linking moieties. In another aspect, a first linking moiety comprising a boron-containing cluster is condensed with a linking moiety lacking a boron-containing cluster. The crystalline product may be either polycrystalline or single crystal. For example, the condensation forms a porous, semicrystalline to crystalline organic materials with high surface areas.

Schemes I and II below show methods for synthesizing 3D and 2D COFs of the disclosure, it is to be understood that each of the rings can comprise additional side groups. In accordance with Scheme 2, the dehydration reaction between phenylboronic acid and 2,3,6,7,10,11-hexahydroxytriphenylene ("HHTP"), a trigonal building block, gives a new 5-membered $BO_2C_2$ ring.

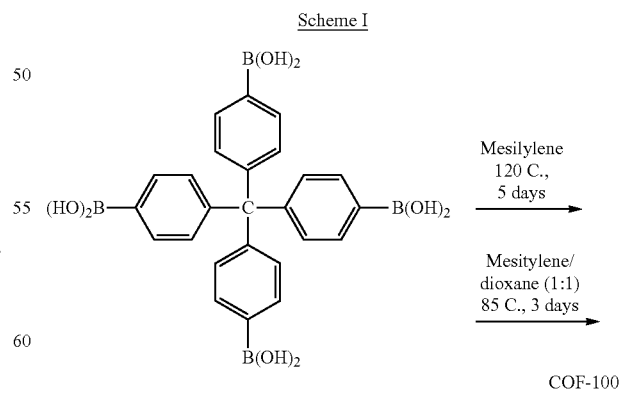

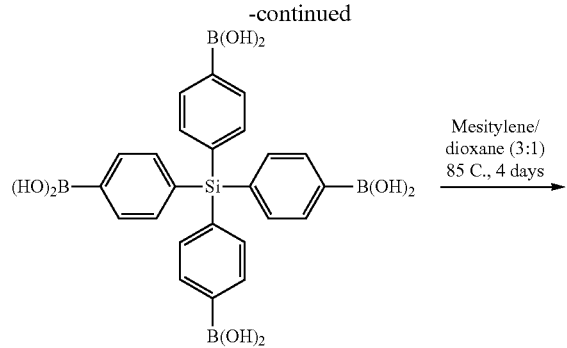
COF-103
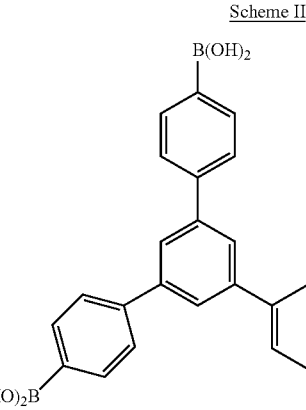
COF-105
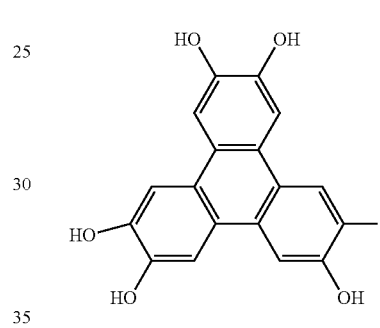
Scheme II
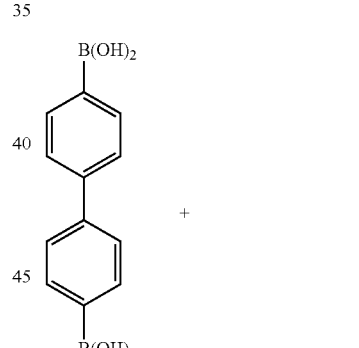
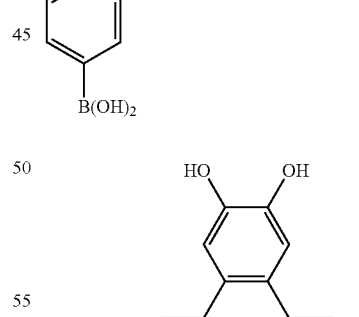
COF-8
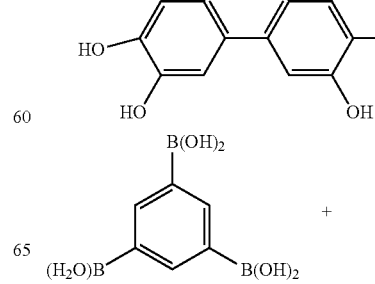
COF-10
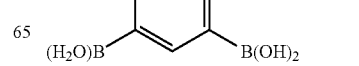

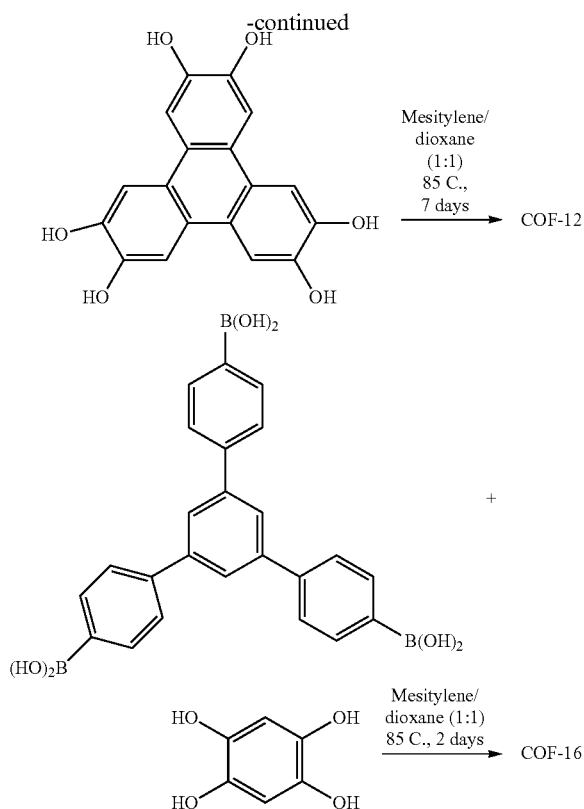

Scheme 2 provides an example of the reaction of BDBA with TBST to form a 3-connected sheet. In an analogous manner as set forth above, the aromatic rings of both the starting materials and products of Scheme 2 are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

The COFs of the disclosure can take any framework/structure. For example, using the methods of the disclosure COFs having any of the following framework type codes can be obtained: ABW ACO AEI AEL AEN AET AFG AFI AFN AFO AFR AFS AFT AFX AFY AHT ANA APC APD AST ASV ATN ATO ATS ATT ATV AWO AWW BCT *BEA BEC BIK BOG BPH BRE CAN CAS CDO CFI CGF CGS CHA CHI CLO CON CZP DAC DDR DFO DFT DOH DON EAB EDI EMT EON EPI ERI ESV ETR EUO EZT FAR FAU FER FRA GIS GIU GME GON GOO HEU IFR IHW ISV ITE ITH ITW IWR IWV IWW JBW KFI LAU LEV LIO LIT LOS LOV LTA LTL LTN MAR MAZ MEI MEL MEP MER MFI MFS MON MOR MOZ MSE MSO MTF MTN MTT MTW MWW NAB NAT NES NON NPO NSI OBW OFF OSI OSO OWE PAR PAU PHI PON RHO RON RRO RSN RTE RTH RUT RWR RWY SAO SAS SAT SAV SBE SBS SBT SFE SFF SFG SFH SFN SFO SGT SIV SOD SOS SSY STF STI STT SZR TER THO TON TSC TUN UEI UFI UOZ USI UTL VET VFI VNI VSV WEI WEN YUG ZON.

A framework on the disclosure may be interpenetrating. Furthermore, where a framework comprises an adsorbed chemical species (e.g., ammonia, carbon dioxide, carbon monoxide, hydrogen, amines, methane, oxygen, argon, nitrogen, argon, organic dyes, polycyclic organic molecules, and combinations thereof) the species may be exchanged or removed prior to reaction with a post framework reactant of the disclosure. The resulting functionalized frameworks (e.g., PRFs) provide useful sensors, absorbant materials, drug delivery devices and the like.

Also provided are devices for the sorptive uptake of a chemical species. The device includes a sorbent comprising a PRF provided herein or obtained by the methods of the disclosure. The uptake can be reversible or non-reversible. In some aspects, the sorbent is included in discrete sorptive particles. The sorptive particles may be embedded into or fixed to a solid liquid- and/or gas-permeable three-dimensional support. In some aspects, the sorptive particles have pores for the reversible uptake or storage of liquids or gases and wherein the sorptive particles can reversibly adsorb or absorb the liquid or gas.

In some embodiments, a device provided herein comprises a storage unit for the storage of chemical species such as ammonia, carbon dioxide, carbon monoxide, hydrogen, amines, methane, oxygen, argon, nitrogen, argon, organic dyes, polycyclic organic molecules, and combinations thereof.

Also provided are methods for the sorptive uptake of a chemical species. The method includes contacting the chemical species with a sorbent that comprises a PRF provided herein. The uptake of the chemical species may include storage of the chemical species. In some aspects, the chemical species is stored under conditions suitable for use as an energy source.

Also provided are methods for the sorptive uptake of a chemical species which includes contacting the chemical species with a device provided described herein.

Natural gas is an important fuel gas and it is used extensively as a basic raw material in the petrochemical and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removal of acid gases from natural gas produced in remote locations is desirable to provide conditioned or sweet, dry natural gas either for delivery to a pipeline, natural gas liquids recovery, helium recovery, conversion to liquefied natural gas (LNG), or for subsequent nitrogen rejection. $CO_2$ is corrosive in the presence of water, and it can form dry ice, hydrates and can cause freeze-up problems in pipelines and in cryogenic equipment often used in processing natural gas. Also, by not contributing to the heating value, $CO_2$ merely adds to the cost of gas transmission.

An important aspect of any natural gas treating process is economics. Natural gas is typically treated in high volumes, making even slight differences in capital and operating costs of the treating unit significant factors in the selection of process technology. Some natural gas resources are now uneconomical to produce because of processing costs. There is a continuing need for improved natural gas treating processes that have high reliability and represent simplicity of operation.

In addition, removal of carbon dioxide from the flue exhaust of power plants, currently a major source of anthropogenic carbon dioxide, is commonly accomplished by chilling and pressurizing the exhaust or by passing the fumes through a fluidized bed of aqueous amine solution, both of which are costly and inefficient. Other methods based on chemisorption of carbon dioxide on oxide surfaces or adsorption within porous silicates, carbon, and membranes have been pursued as means for carbon dioxide uptake.

However, in order for an effective adsorption medium to have long term viability in carbon dioxide removal it should combine two features: (i) a periodic structure for which carbon dioxide uptake and release is fully reversible, and (ii) a flexibility with which chemical functionalization and molecular level fine-tuning can be achieved for optimized uptake capacities.

A number of processes for the recovery or removal of carbon dioxide from gas steams have been proposed and practiced on a commercial scale. The processes vary widely, but generally involve some form of solvent absorption, sponding alcohol derivative, and converted to an imine functionality in refluxing methanol (Scheme III). Despite these strong reaction conditions, the integrity of the ZIF structure and its crystallinity are maintained throughout the synthesis. The isolated ZIF derivatives indicate that those organic reactions proceeded in high conversions. In essence the success in achieving typical organic reactions in crystals of extended structures like ZIFs makes the idea of using the "crystal as a molecule" a reality and opens many opportunities for employing the arsenal of organic reactions in the covalent functionalization of extended structures.

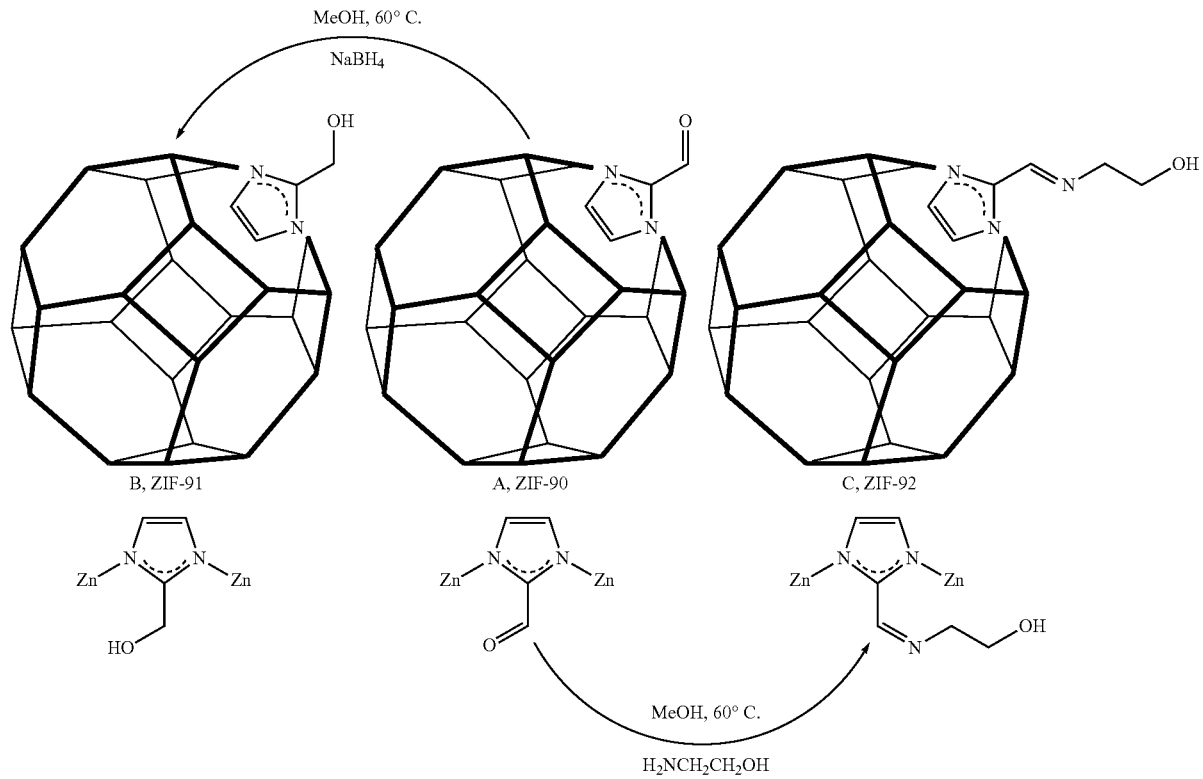

Scheme III adsorption on a porous adsorbent, distillation, or diffusion through a semipermeable membrane.

Examples

The methods provided herein extended to zeolitic imidazolate frameworks (ZIFs) as well as other frameworks, which have unusual thermal and chemical stability, and thus are ideal platforms for performing useful organic transformations under strong reaction conditions. Methods of generating porous ZIFs, COFs, MOFs and BOFs are described herein. To perform the postsynthesis functionalization on crystals, solvent guest species in the as-synthesized ZIFs, COFs, MOFs and BOFs are removed by immersing the crystals in a polar solvent such as methanol, related alkanols (e.g., ethanol and butanol) and related compounds such as chloromethane and methoxymethane. The solvent is then evacuated. The links in the framework (e.g., the imidazolate-2-carboxaldehyde (ICA) links, which join tetrahedral zinc (II) centers in a ZIF) are reduced by $NaBH_4$ to the corre- A new crystalline ZIF structure (termed ZIF-90, FIG. 1) was synthesized by heating a solution mixture of H—ICA and $Zn(NO_3)_2.4H_2O$ (3:2 mol ratio) in N,N-dimethylformamide (DMF) at 100° C. for 18 h. The same material can also be obtained by diffusion of a triethylamine and hexane solution into a DMF mixture of H—ICA and $Zn(NO_3)_2.4H_2O$ at 25° C. for 24 h. Elemental analysis performed on guest free ZIF-90 gave the expected formula, $Zn(C_4H_3N_2O)_{2.4}$ Crystals of as-synthesized ZIF-90 where examined by single crystal X-ray diffraction (XRD) techniques and the structure was found to be related to the sodalite topology ($SiO_2$, sod, FIG. 1A-C) by replacing the Si and O with Zn(II) and ICA links, respectively. This leads to an expanded ZIF structure with large voids (FIG. 1B) and an extended 3-D ZIF structure with an aperture of 3.5 Å in diameter and a pore size of 11.2 Å (FIG. 1C). To perform the postsynthesis functionalization on crystals of ZIF-90, its porosity and structural integrity were examined. Solvent guests in the as-synthesized form of ZIF-90 were removed by first immersing the crystals in methanol then evacuating (0.01 Torr) at 25° C. for 24 h. The $N_2$ adsorption isotherm for the resulting sample measured at 77 K (FIG. 2) showed a steep rise in the low-pressure region indicating the permanent porosity of the ZIF-90 framework.

The small step at higher pressure with a hysteresis loop is attributed to a slight constriction of the pores due to the presence of the aldehyde functionality on the ICA links. Nevertheless, this does not prevent access to the pores by $N_2$ molecules, and thus the calculated Langmuir and BET surface areas from the adsorption data for ZIF-90 were 1320 and 1270 $m^2/g$, respectively.

Thermogravimetric analysis on the evacuated framework of ZIF-90 showed a plateau region of no significant weight loss in the temperature range 300-500° C. Furthermore, the high chemical stability of ZIF-90 was evidenced by the unaltered powder X-ray diffraction (PXRD) patterns upon boiling the solid in water, toluene, and methanol for 24 h. To ensure that the bulk crystals of ZIF-90 possess aldehyde functionality, the solid state, $^{13}C$ cross polarization magic angle spinning (CP/MAS) NMR and FTIR spectra were measured. The $^{13}C$ CP/MAS NMR spectrum showed the expected resonances at 129, 150, and 178 ppm for the symmetrically equivalent 4- and 5-carbon atoms of the imidazolate, the 2-carbon atom of the imidazolate and the aldehyde carbon atom, respectively. A strong band at 1678 cm-1 (vCdO) observed in the FTIR spectrum provided further evidence for the presence of aldehyde in bulk ZIF-90 samples.

Figure 3:
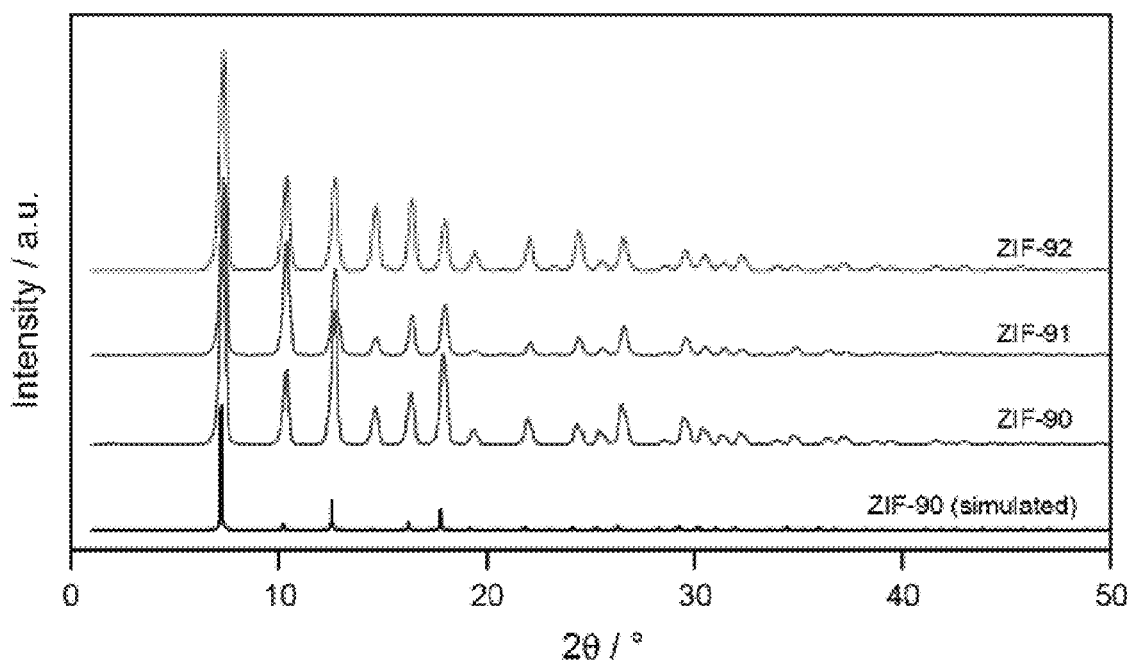
FIG. 3 shows PXRD patterns of simulated ZIF-90 (black), ZIF-90 (bottom), ZIF-91 (middle), and ZIF-92 (top).
Figure 4:
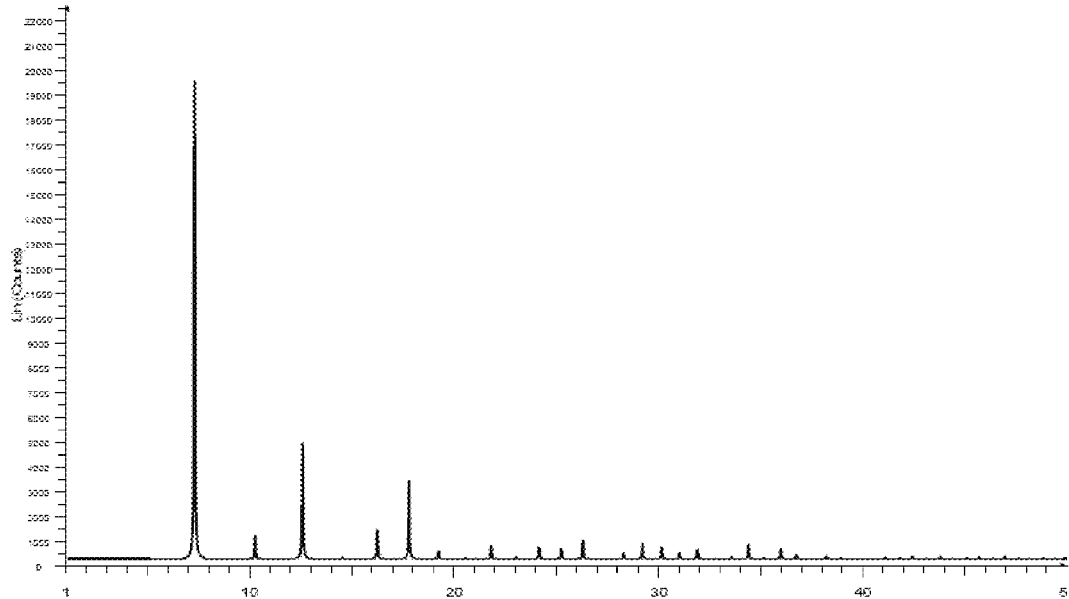
FIG. 4 shows simulated PXRD pattern from ZIF-90 single crystal.
Figure 5:
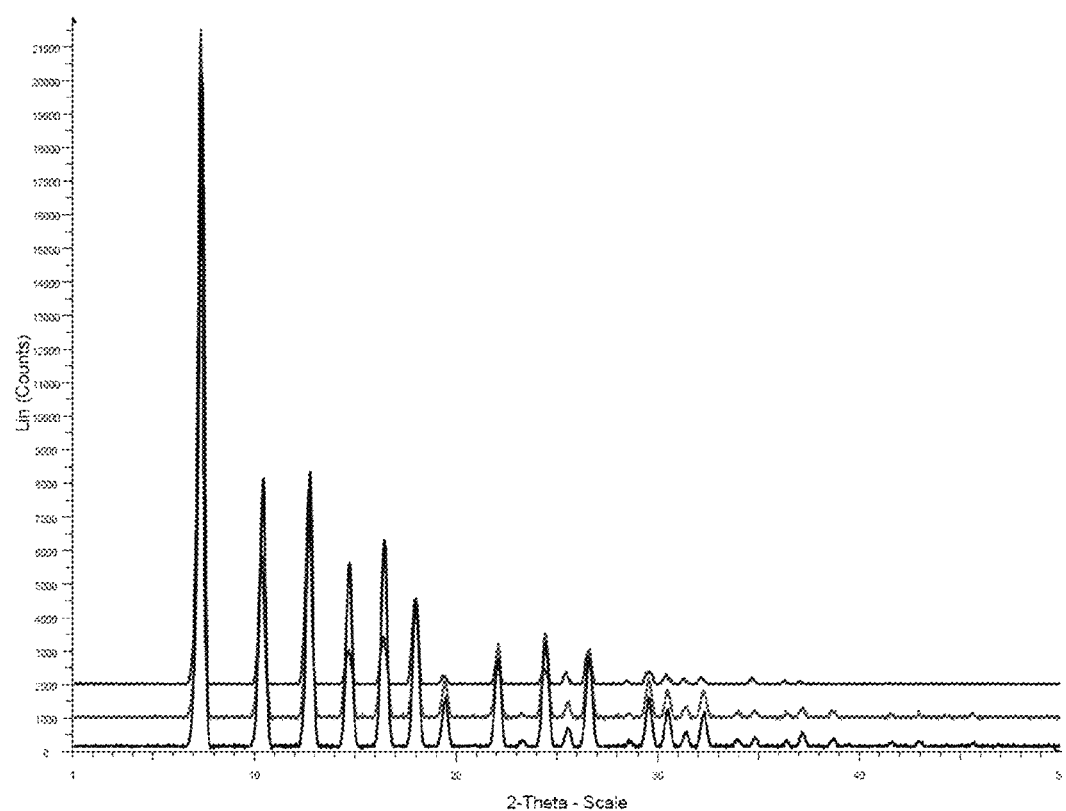
FIG. 5 shows PXRD patterns of evacuated ZIF-90 (top), Solvent exchanged (middle) and as synthesized (bottom).
Figure 6:
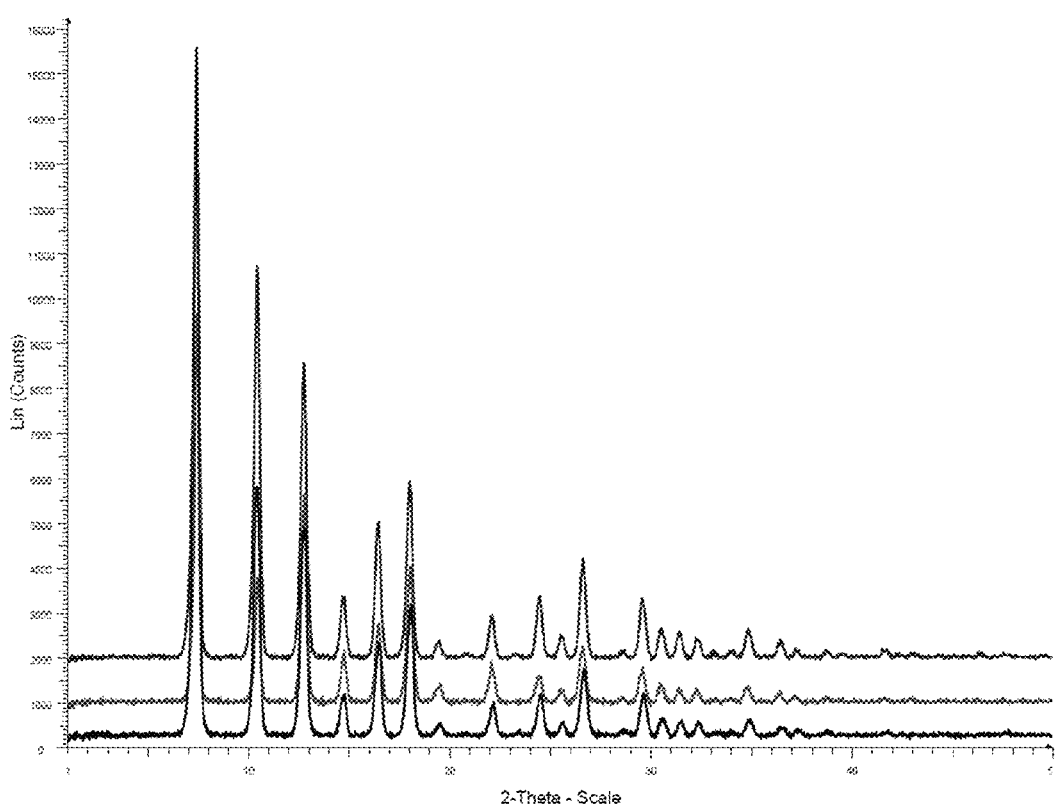
FIG. 6 shows PXRD patterns of evacuated ZIF-91 (top), Solvent exchanged (middle) and as synthesized (bottom).
Figure 7:
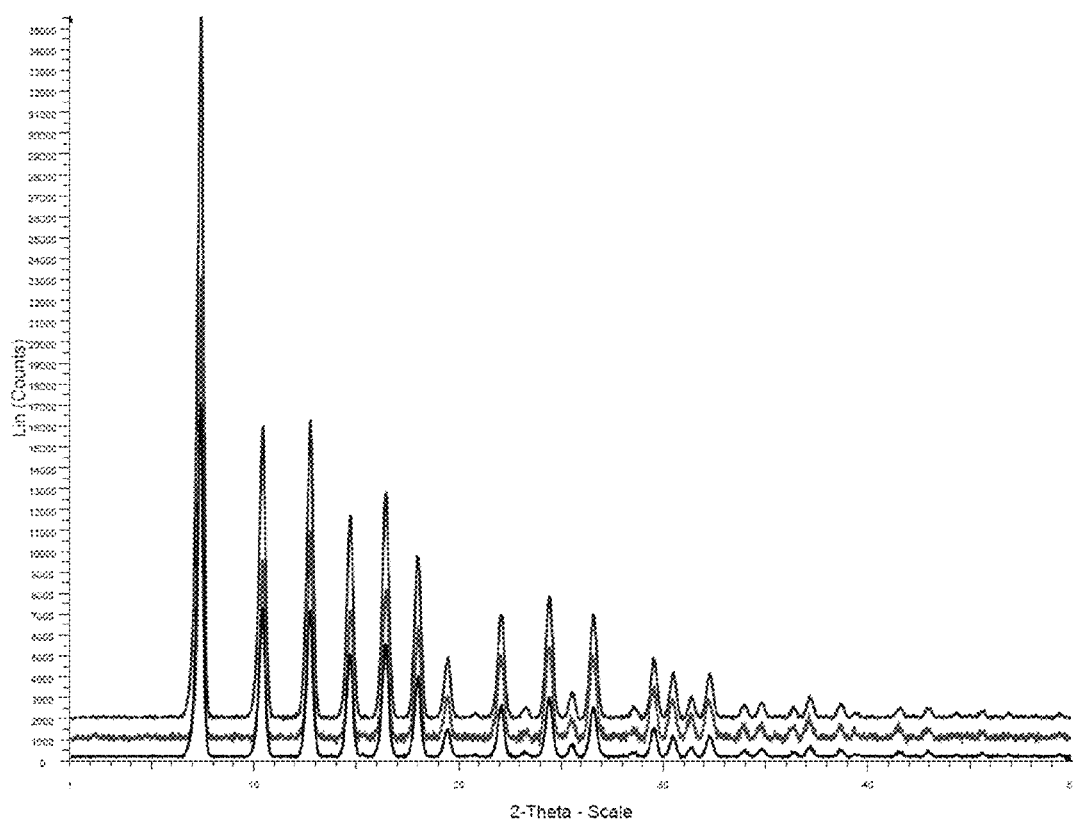
FIG. 7 shows PXRD patterns of evacuated ZIF-92 (top), Solvent exchanged (middle) and as synthesized (bottom).
Figure 8:
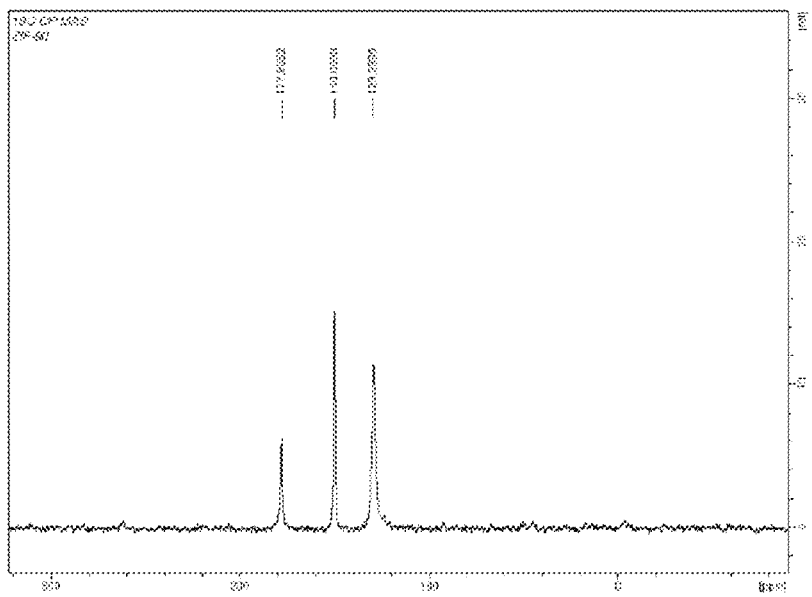
FIG. 8 shows solid-state $^{13}C$ CP/MAS spectrum of ZIF-90.
Figure 9:
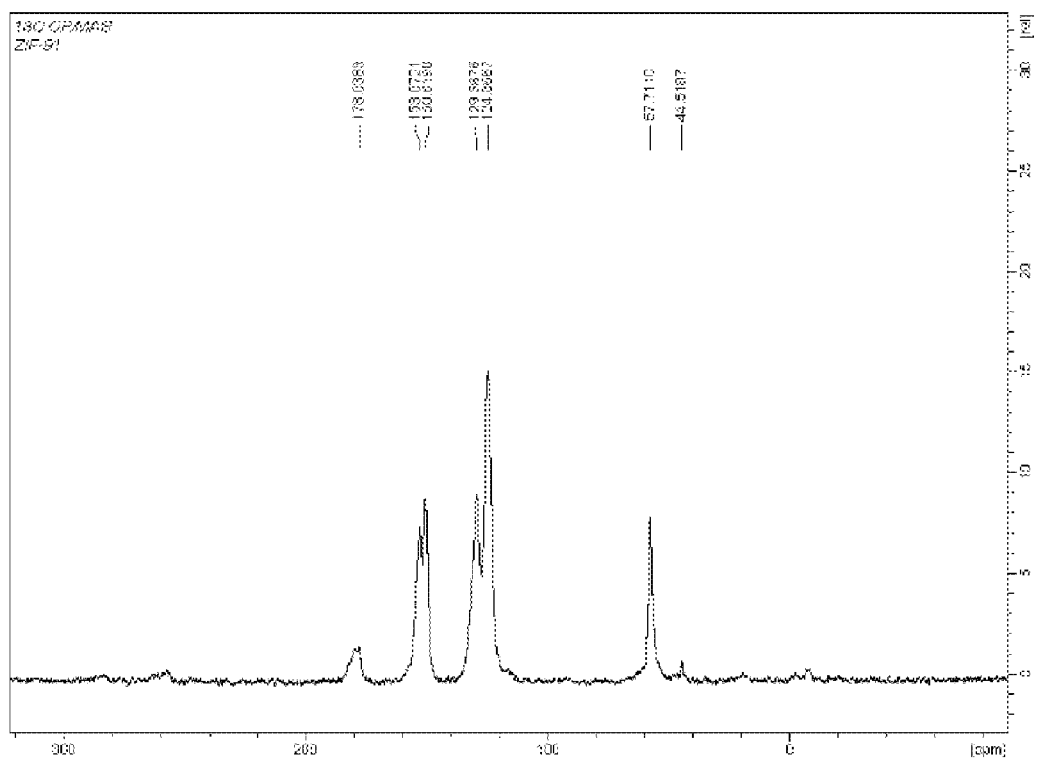
FIG. 9 shows solid-state $^{13}C$ CP/MAS spectrum of ZIF-91.
Figure 10:
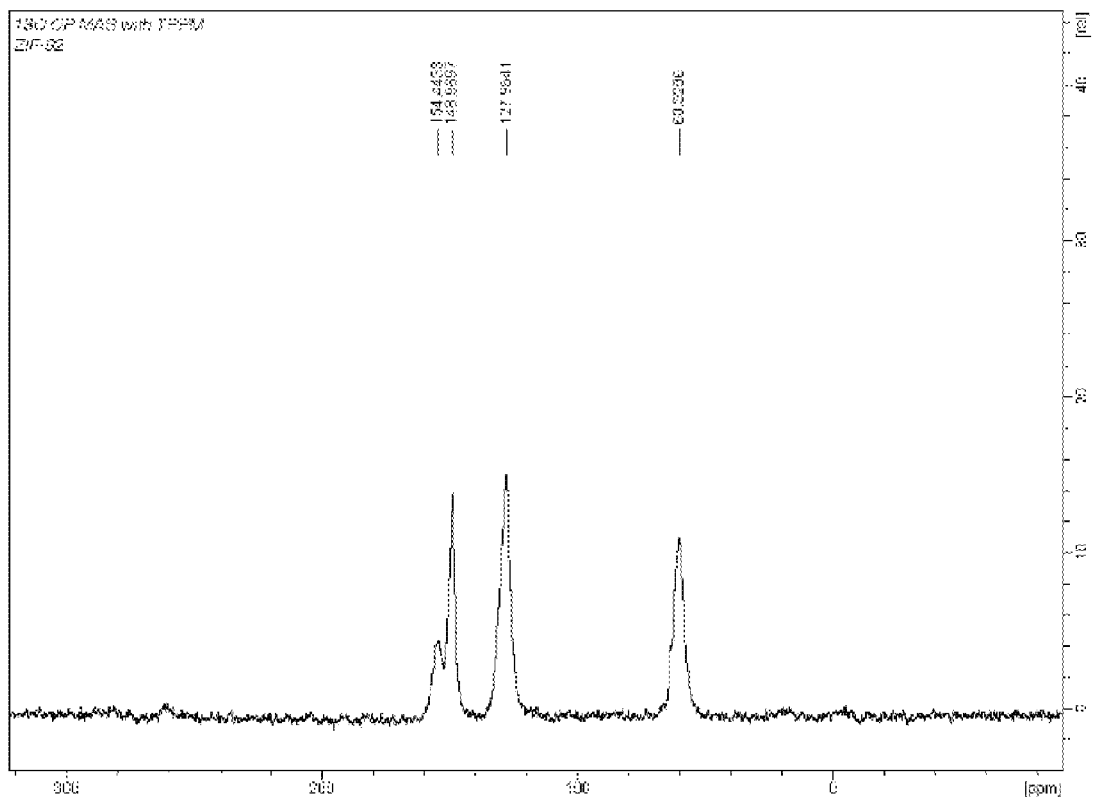
FIG. 10 shows solid-state $^{13}C$ CP/MAS spectrum of ZIF-92.
Figure 11:
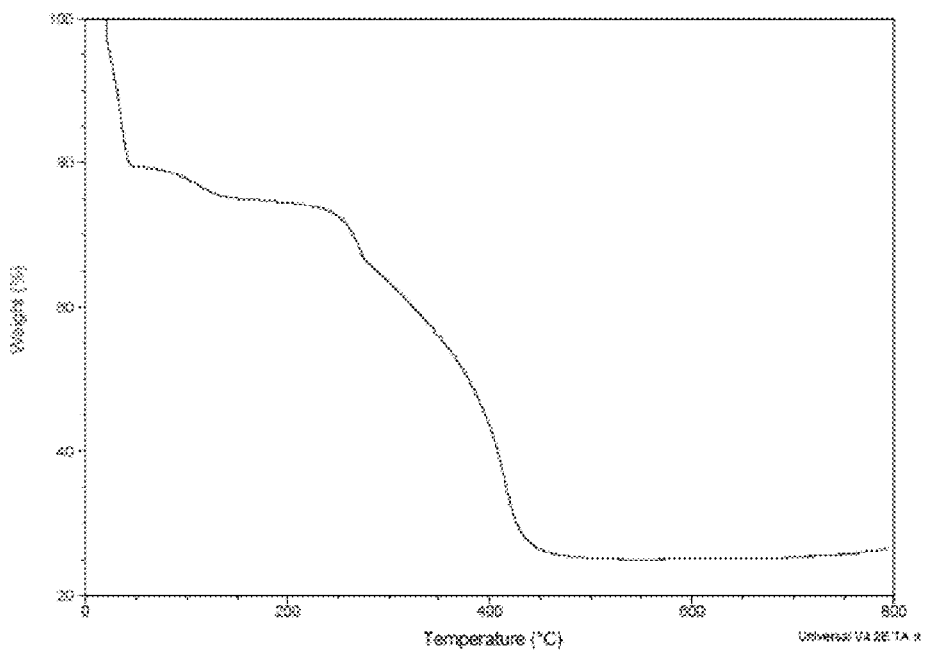
FIG. 11 shows a TGA trace of as synthesized ZIF-90 after washing in methanol.
Figure 12:
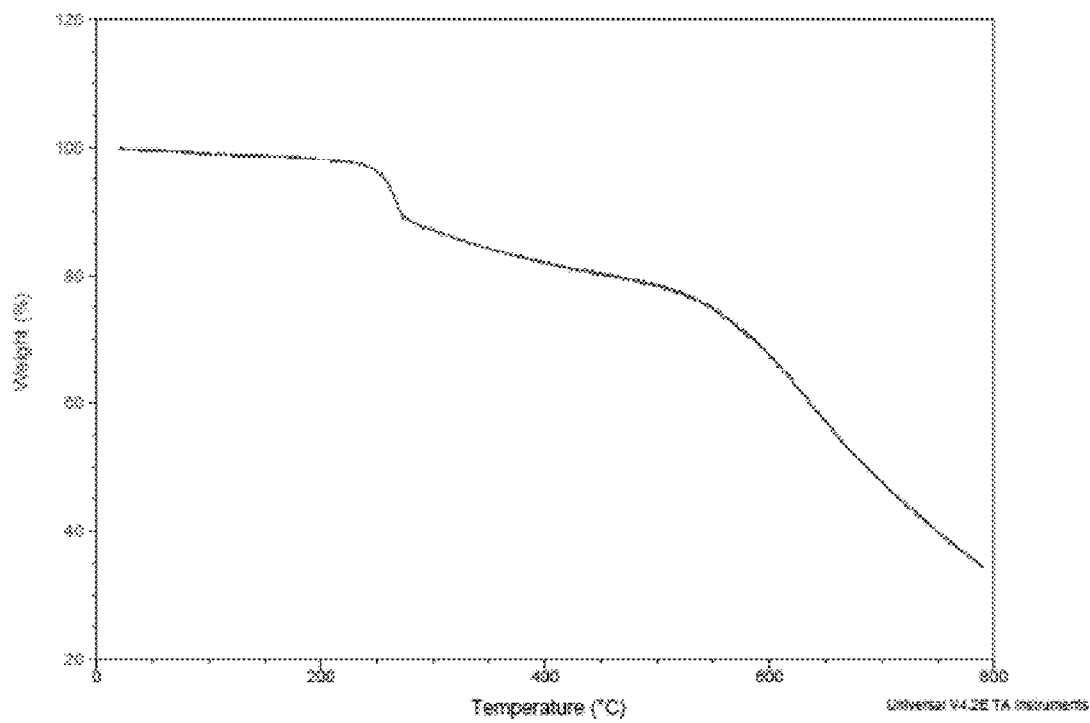
FIG. 12 shows a TGA trace of evacuated ZIF-90.
Figure 13:
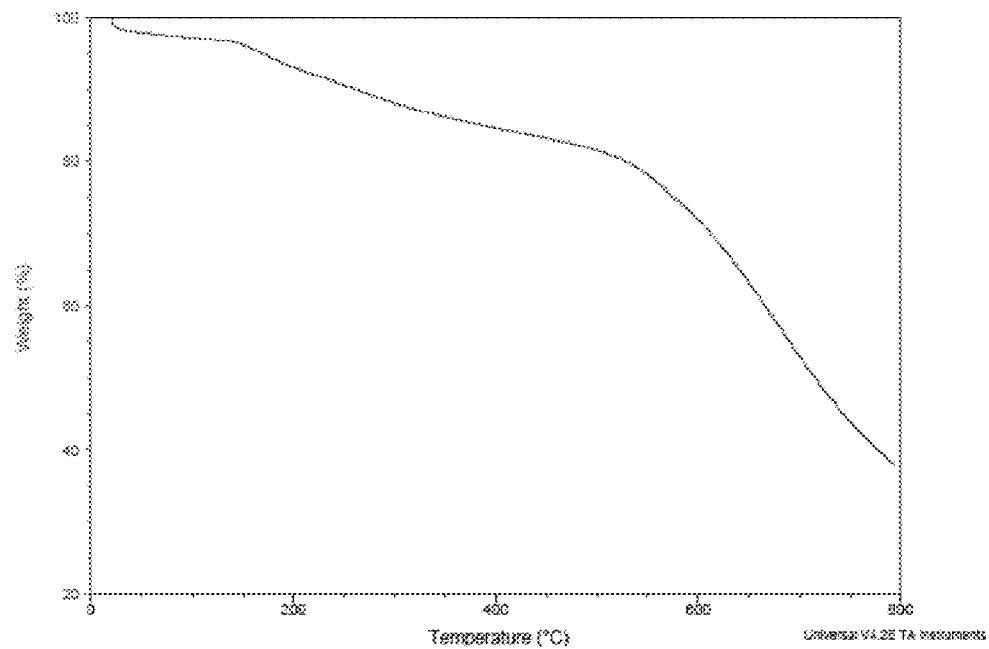
FIG. 13 shows a TGA trace of evacuated ZIF-91. The initial weight loss 50-150° C. is due to methanol trapped within the pores. Furthermore, the loss of weight 150-300° C. is most likely due to strongly associated solvent within the framework. ZIF-91 remains crystalline at 200° C.
Figure 14:
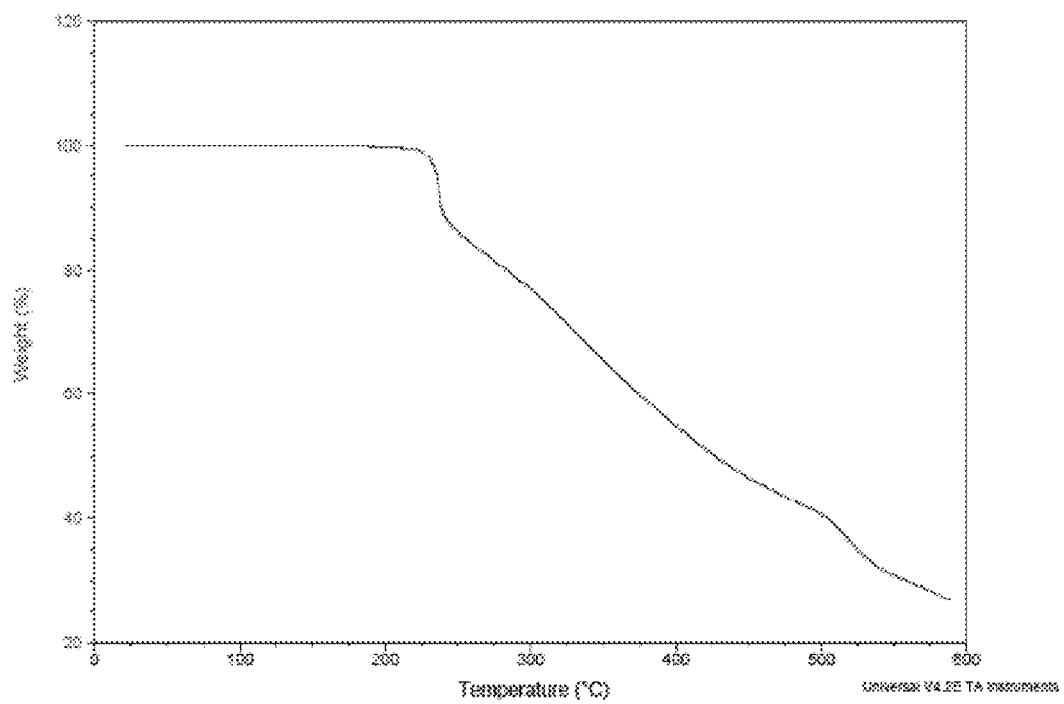
FIG. 14 shows a TGA trace of evacuated ZIF-92. The plateau (0-250° C.) TGA trace of ZIF-92 may be attributed to the imine functionality occluding the pores. Thus no solvent loss is observed until approximately 250° C. as it would be trapped within the pores. The liberation of solvent and constant loss of weight from 250 to 500° C. most probably results from the destruction of the framework. ZIF-92 remains crystalline at 100° C. but losses crystallinity at 200° C.
Figure 15:
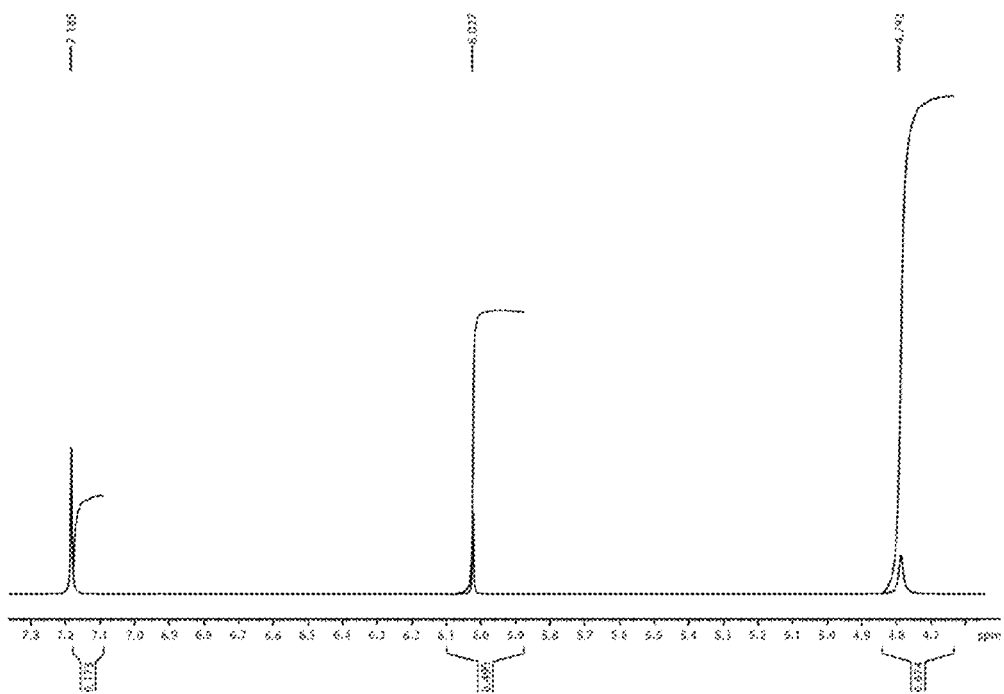
FIG. 15 shows an NMR spectrum for digested ZIF-90. (500 MHz, 20% $DCl/D_2O$) δH 7.2 ppm (2H, s, CH-imidazole ring), (1H, s, CCHO), 4.79 ppm ($D_2O$).

Given the permanent porosity of ZIF-90 and its exceptional chemical stability, useful organic transformations were performed on its evacuated crystalline samples. Specifically, reduction of aldehyde to alcohol functionality was successfully achieved by reacting ZIF-90 with $NaBH_4$ in methanol at 60° C. for 24 h to give ZIF-91 (Scheme III B). Remarkably, ZIF-91 maintained the high crystallinity of the parent framework (ZIF-90) as confirmed by their coincident PXRD patterns (FIG. 3). The presence of the alcohol group in ZIF-91 bulk samples was revealed by $^{13}C$ CP/MAS NMR spectroscopy. This showed the appearance of four imidazolate carbon atom resonances suggesting that two chemically distinct imidazolate links were present within the framework. Furthermore, the observation of peaks attributable to both aldehyde and alcohol functional groups indicated that reduction was incomplete. To quantify the extent of reduction, a sample of ZIF-91 was digested in 20% $DCl/D_2O$ and analyzed by solution $^1H$ NMR. Comparison between the integrated peak intensities of the reduced and unreduced imidazolate species indicated that approximately 80% conversion had been achieved. In addition, confirmation of covalent modification was demonstrated by electrospray ionization mass spectrometry performed on samples of digested ZIF-91. The observation of peaks at 95.2 and 97.3 m/z were consistent with the negative parent ions of the aldehyde and alcohol functionalized imidazole links, respectively.

Figure 2:
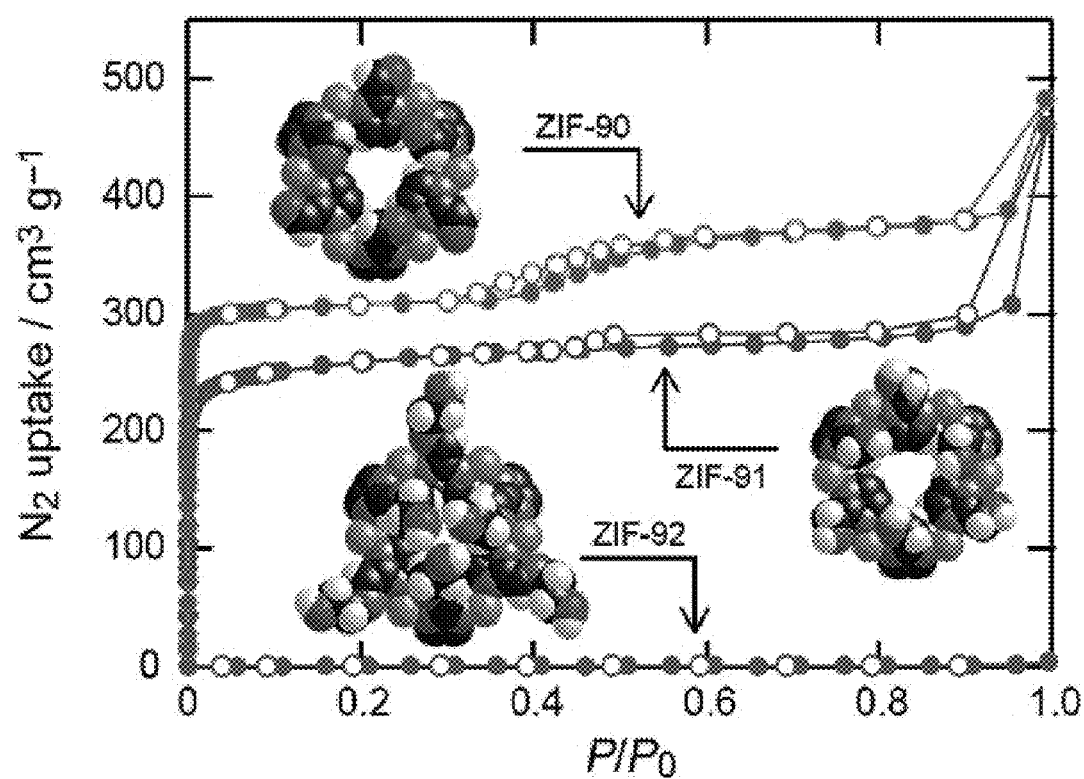
FIG. 2 shows an $N_2$ isotherms of ZIF-90 (top), ZIF-91 (middle), and ZIF-92 (bottom) measured at 77 K. ZIF-90, 91, and 92 pore apertures are shown as space filled representations.

It is worthy to note that porosity of ZIF crystals was maintained throughout the conversion reaction of ZIF-90 to ZIF-91 (surface area of ZIF-91: 1070 and 1010 $m^2g^{-1}$ for Langmuir and BET surface areas, respectively). The observed slight decrease in surface area may be due to the smaller pore aperture of ZIF-91 relative to that of ZIF-90 (FIG. 2).

The chemical versatility of the aldehyde group was highlighted by performing another organic transformation on the ICA link of ZIF-90. Reaction of ZIF-90 with ethanolamine in methanol at 60° C. gave ZIF-92 (Scheme III C). Quantitative conversion to the imine was completed within three hours as verified by $^{13}C$ CP/MAS NMR and FTIR. The $^{13}C$ solid state NMR spectrum of ZIF-92 showed resonances at 154 and 60 ppm for the imine and methylene carbons and resonances at 149 and 128 ppm for the imidazolate carbon atoms. A complete absence of any resonances due to ZIF-90 confirmed the quantitative imine formation of ZIF-92. Additionally, the FTIR spectrum of ZIF-92 was devoid of the vCdO stretching frequency at 1678 $cm^{-1}$ and showed the appearance of a peak at 1637 $cm^{-1}$ due to the vCdN bond of the imine. As was the case for the conversion of ZIF-90 to ZIF-91, the high crystallinity of the ZIF structure was maintained as evidenced by the PXRD pattern of ZIF-92 (FIG. 3). The presence of the imine functionality in ZIF-92 severely constricts the pore aperture and prevents N2 molecules from accessing the interior of the pores, as confirmed by its gas adsorption isotherm behavior (FIG. 2).

All reagents unless otherwise stated were obtained from commercial sources (Alfa Aesar, Cambridge isotope laboratories, Sigma Aldrich) and were used without further purification. Yields reported were unoptimized. Elemental microanalyses were performed on a Thermo Flash EA1112 combustion CHNS analyzer.

Synthetic Procedure for ZIF-90.

Solvothermal procedure. Single crystals of ZIF-90 were obtained by heating a solution of zinc nitrate tetrahydrate $(Zn(NO_3)_2.4H_2O)$ (0.054 g, 0.21 mmol) and imidazole-2-carboxaldehyde (0.029 g, 0.30 mmol) in N,N-dimethylformamide (DMF, 3 mL) for 18 h at 100° C.

Vapor Diffusion.

Zinc nitrate tetrahydrate $(Zn(NO_3)_2.4H_2O)$ (0.13 g, 0.50 mmol) and imidazole-2-carboxaldehyde (0.07 g, 0.75 mmol) in DMF (10 mL) was placed in a desiccator under an atmosphere of triethylamine (5 mL) in hexane (200 mL). The reaction was allowed to sit at room temperature for 24 h. The crystalline powder obtained was filtered and washed with methanol (3×5 mL). The product was activated with methanol (3×10 mL) over a three-day period before being dried under vacuum ($10^{-2}$ Torr) for 24 h at room temperature. Yield (0.08 g, 61.5%) CHN calculated for C8H6N4O2Zn: C, 37.60; H, 2.37; N, 21.92% Found: C, 37.63; H, 2.76; N, 20.48%.

Procedure for Covalent Post Synthetic Modification of ZIF-91 and ZIF-92 are as Follows.

ZIF-91 $Zn(C_4H_3N_2O)_{0.4}(C_4H_5N_2O)_{1.6}$. Dried ZIF-90 crystals (0.10 g, 0.39 mmol) were suspended in methanol (10 mL) and $NaBH_4$ (0.06 g, 1.56 mmol), and refluxed for 24 h. The reaction mixture was filtered and the solid was washed 2-3 times with fresh methanol (20 mL). The microcrystalline solid was further exchanged with fresh methanol (20 mL) for 24 h. The solid was dried under vacuum ($10^{-2}$ Torr) for 24 h at room temperature. Yield (0.09 g, 89%), conversion 77%. It is worth noting that higher conversion of ZIF-90 to ZIF-91 may be achieved through reaction times exceeding 24 h, however, a reduction in crystallinity is observed.

ZIF-92 $Zn(C_6H_8N_3O)_2$.

Dried ZIF-90 crystals (0.15 g, 0.59 mmol) was suspended in methanol (10 mL) and ethanolamine (0.11 mL, 1.76 mmol), and refluxed for 24 hours. The reaction mixture was filtered and the solid was washed 2-3 times with fresh methanol (20 mL). The solid was further exchanged with fresh methanol (20 mL) for 24 h. The solid was dried under vacuum ($10^{-2}$ Torr) for 24 h at room temperature. Yield (0.16 g, 80%), conversion 100%.

Powder X-Ray Diffraction.

Powder X-ray data were collected using a Bruker D8-Discover θ-2θ diffractometer in reflectance Bragg-Brentano geometry employing Ni filtered Cu Kα line focused radiation at 1600 W (40 kV, 40 mA) power and equipped with a Vantec Line detector. Radiation was focused using parallel focusing Gobel mirrors. The system was also outfitted with an anti-scattering shield that prevents incident diffuse radiation from hitting the detector, preventing the normally large background at 2θ<3. Samples were mounted on zero background sample holders by dropping powders from a wide-blade spatula and then leveling the sample with a razor blade.

Solid State 13C CP/MAS Nuclear Magnetic Resonance Spectroscopy.

High resolution solid-state nuclear magnetic resonance (NMR) spectra were recorded at ambient pressure on a Bruker DSX-300 spectrometer using a standard Bruker magic angle-spinning (MAS) probe with 4 mm (outside diameter) zirconia rotors. The magic angle was adjusted by maximizing the number and amplitudes of the signals of the rotational echoes observed in the 79Br MAS FID signal from KBr. Cross-polarization with MAS (CP/MAS) was used to acquire 13C data at 75.47 MHz. The $^1$H and $^{13}$C ninety-degree pulse widths were both 4 ms. The CP contact time varied from 1.5 to 5 ms. High power two-pulse phase modulation (TPPM) 1H decoupling was applied during data acquisition. The decoupling frequency corresponded to 72 kHz. The MAS sample-spinning rate was 10 kHz. Recycle delays between scans varied between 3 and 10 s, depending upon the compound as determined by observing no apparent loss in the $^{13}$C signal from one scan to the next. The 13C chemical shifts are given relative to tetramethylsilane as zero ppm, calibrated using the methylene carbon signal of adamantane assigned to 37.77 ppm as secondary reference.

Thermalgravimetry.

Samples were run on a TA instrument Q-500 series thermal gravimetric analyzer (TGA) with samples held in platinum plans under nitrogen. A 5 K/min ramp rate was used.

Solution NMR $^1$H Nuclear Magnetic Resonance Spectroscopy.

Figure 16:
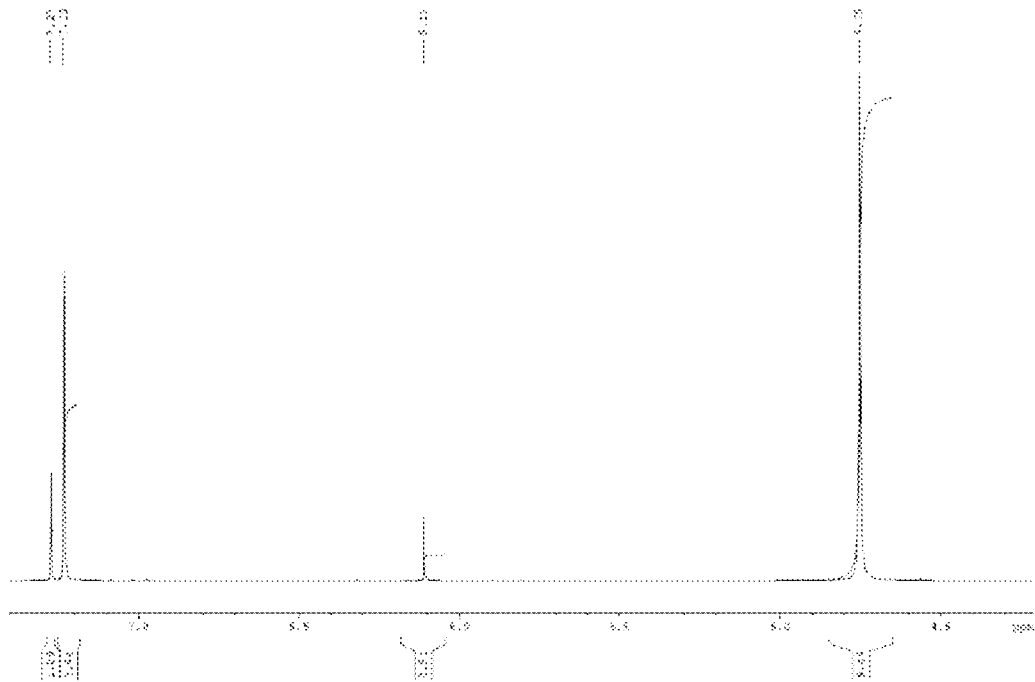
FIG. 16. NMR spectrum for digested ZIF-91. (500 MHz, 20% $DCl/D_2O$) δH 7.31 ppm (2H, s, CH-imidazole ring aldehyde), 7.27 ppm (2H, s, CH-imidazole ring alcohol) (1H, s, CCHO), 4.79 ppm ($D_2O$).
Figure 17:
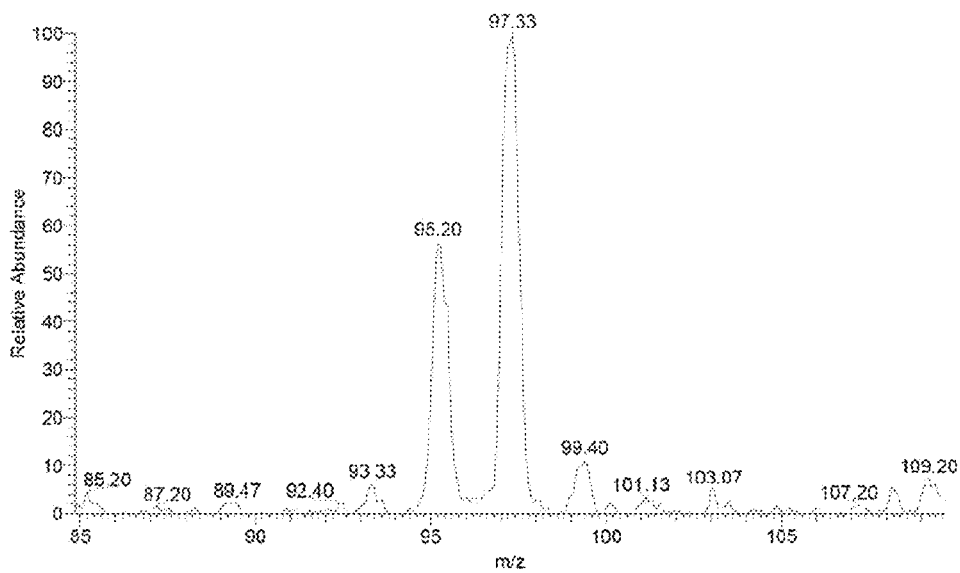
FIG. 17 shows an ESI mass spectrum of ZIF-91.
Figure 18:
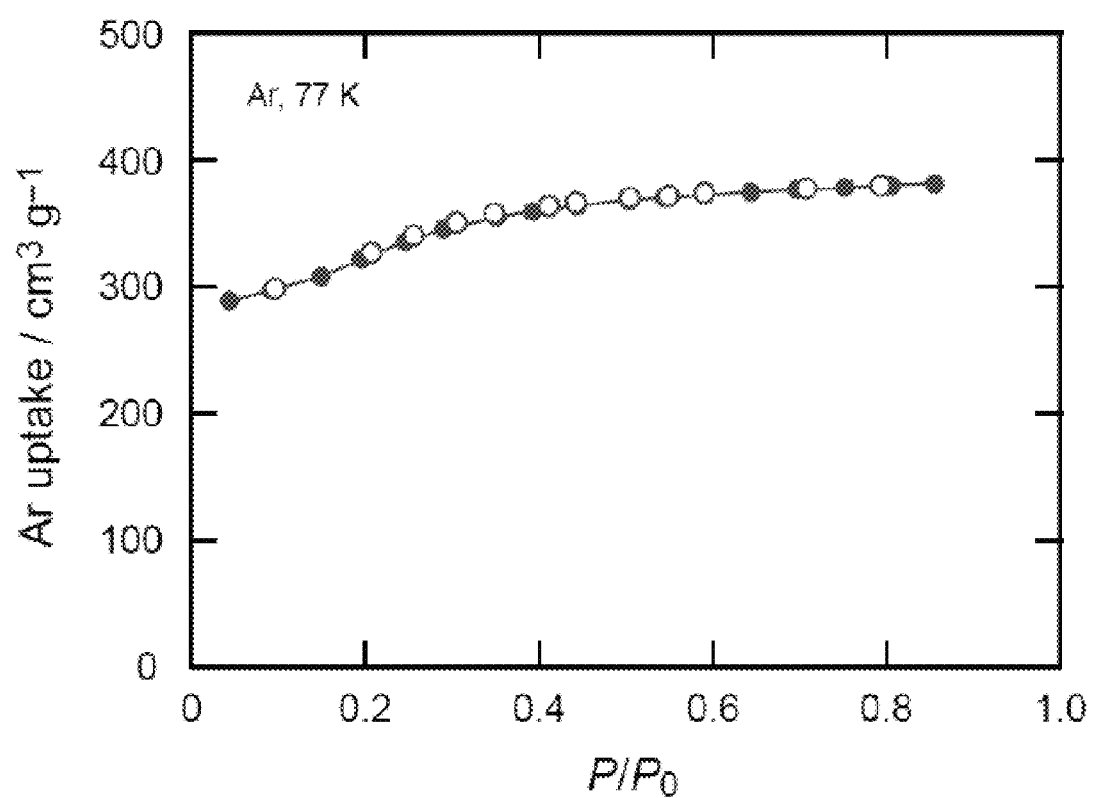
FIG. 18 shows Ar isotherms for ZIF-90 measured at 77 K. No step with a significant hysteresis was observed, which indicates that ZIF-90 does not have a mesopore. Filled and open circles represent adsorption and desorption branch, respectively. Connecting trace is guide for eyes.
Figure 19:
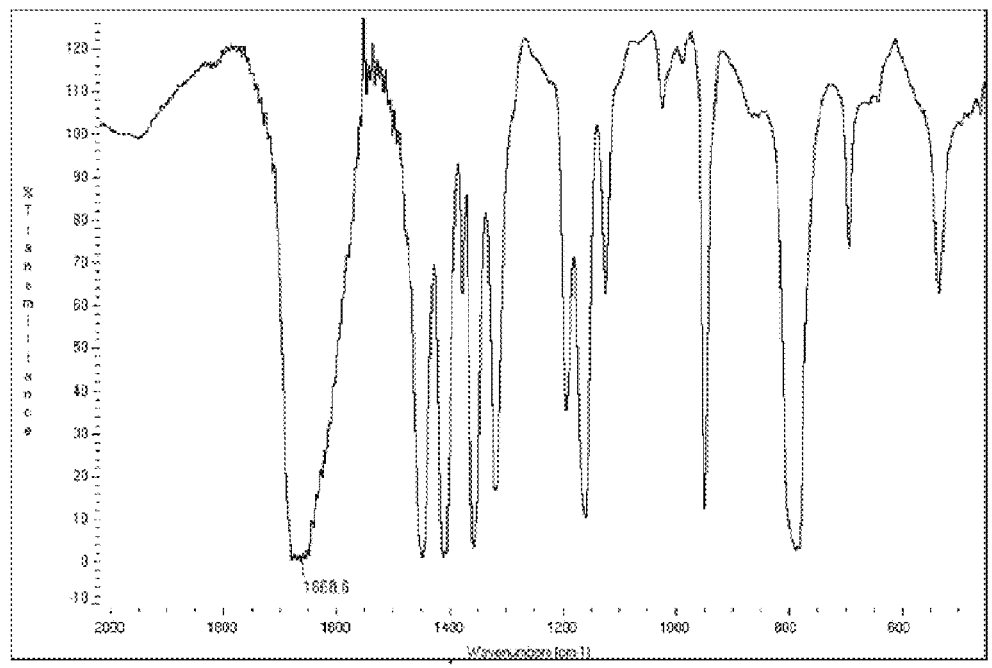
FIG. 19 shows ZIF-90 aldehyde stretch at 1668 $cm^{-1}$ highlighted for clarity.
Figure 20:
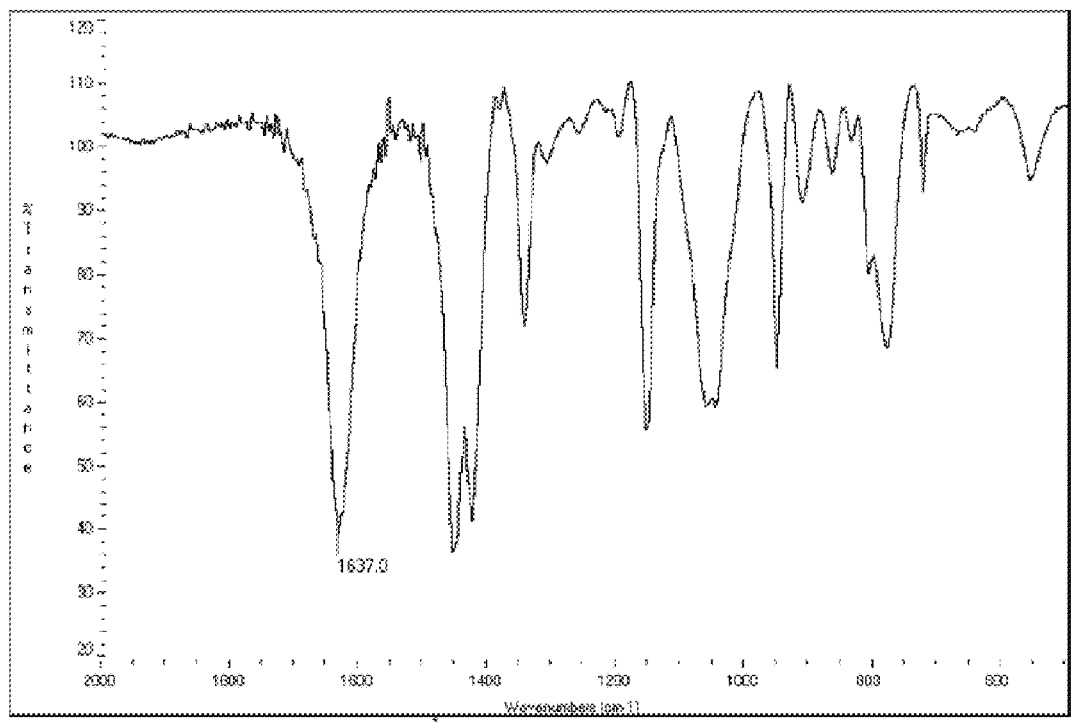
FIG. 20 shows a ZIF-92 imine stretch at 1637 $cm^{-1}$ highlighted for clarity.
Figure 21:
FIG. 21 is a representative optical photographs of ZIF-90 (0.1 mm) found in vials after solvothermal process.
Figure 22:
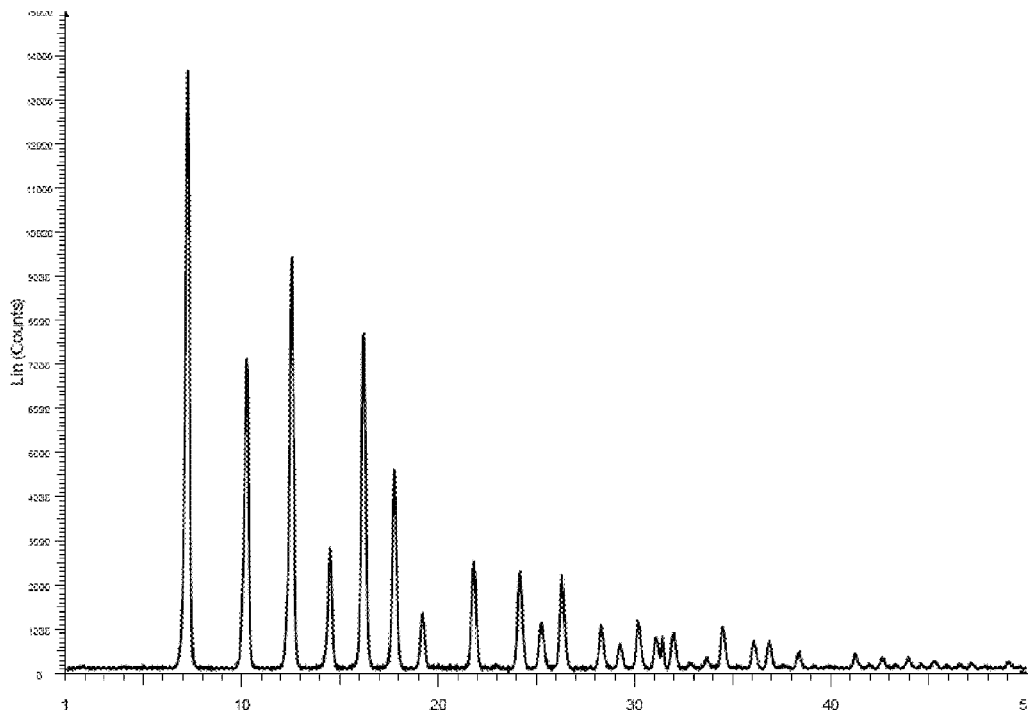
FIG. 22 shows a PXRD pattern of ZIF-90 boiled in toluene 24 h.
Figure 23:
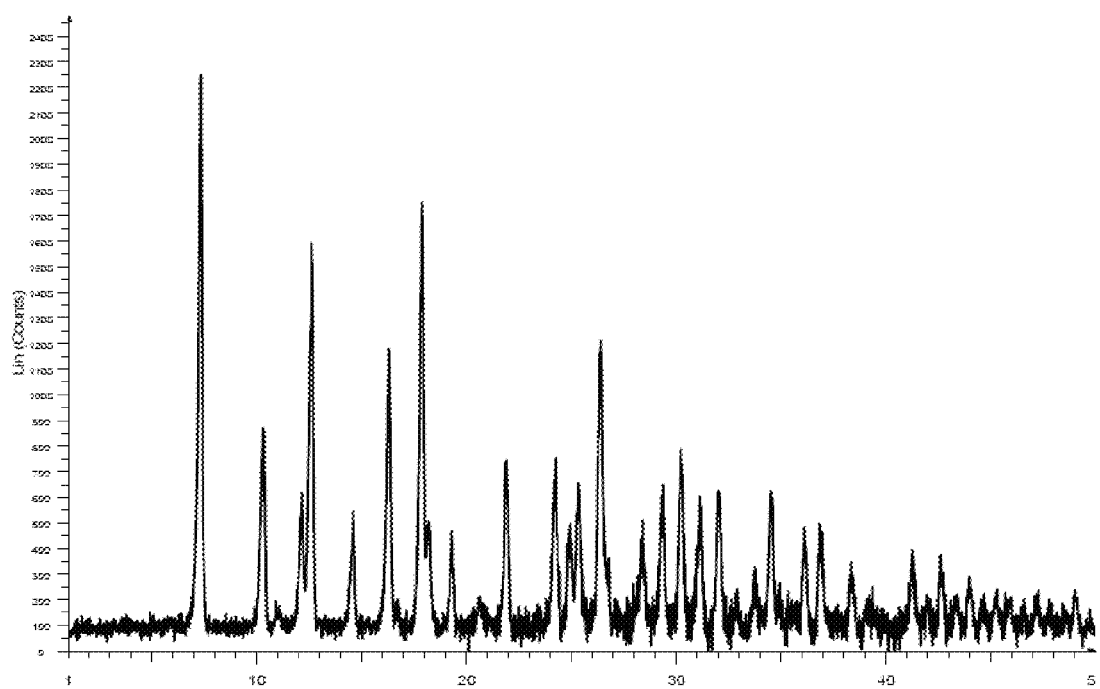
FIG. 23 shows PXRD pattern of ZIF-90 boiled in water 24 h.
Figure 24:
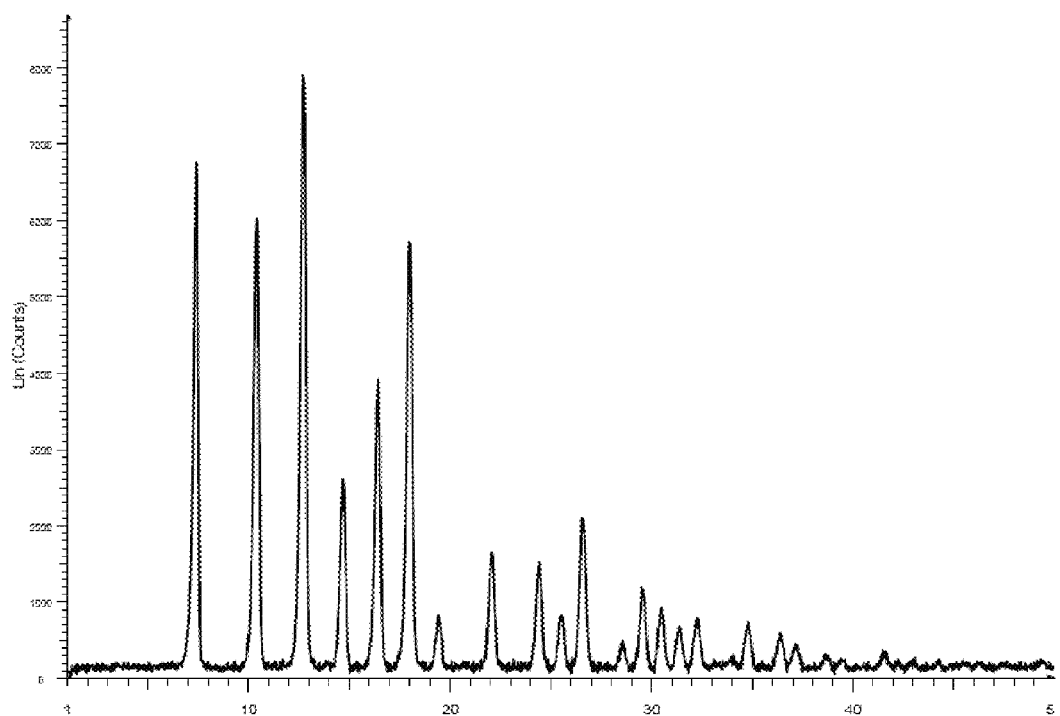
FIG. 24 shows PXRD pattern of ZIF-90 boiled in methanol 24 h.
Figure 25:
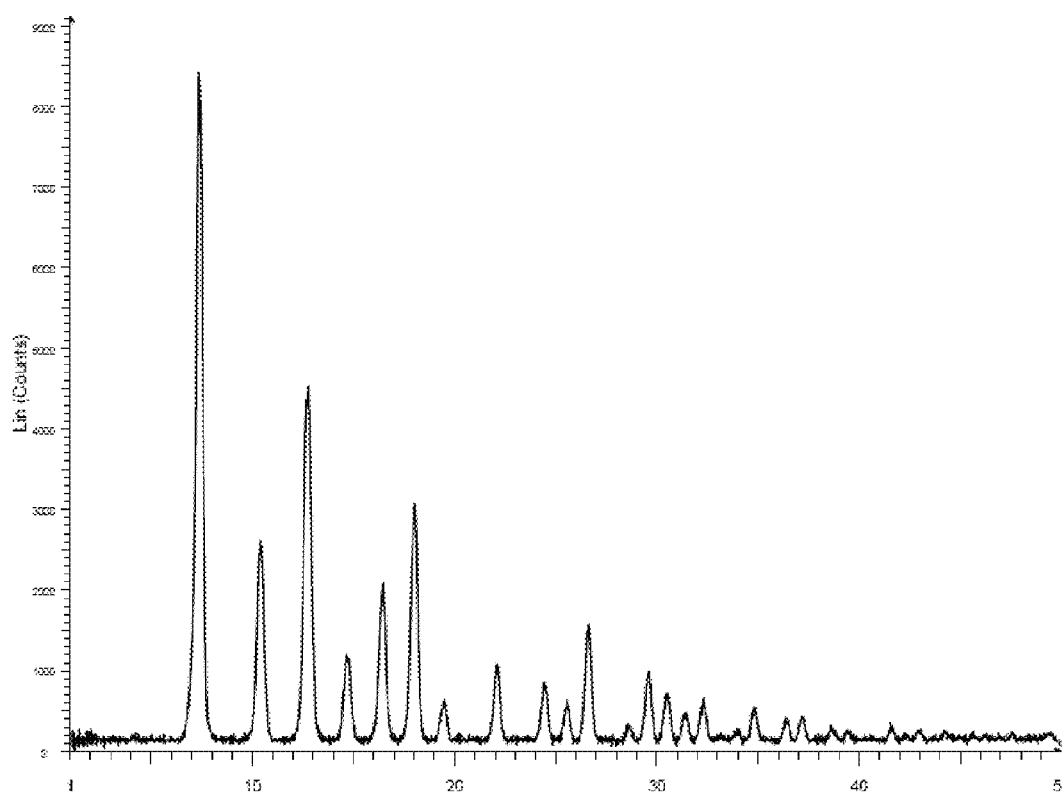
FIG. 25 shows PXRD pattern of ZIF-90 after heating to 250° C.
Figure 26:
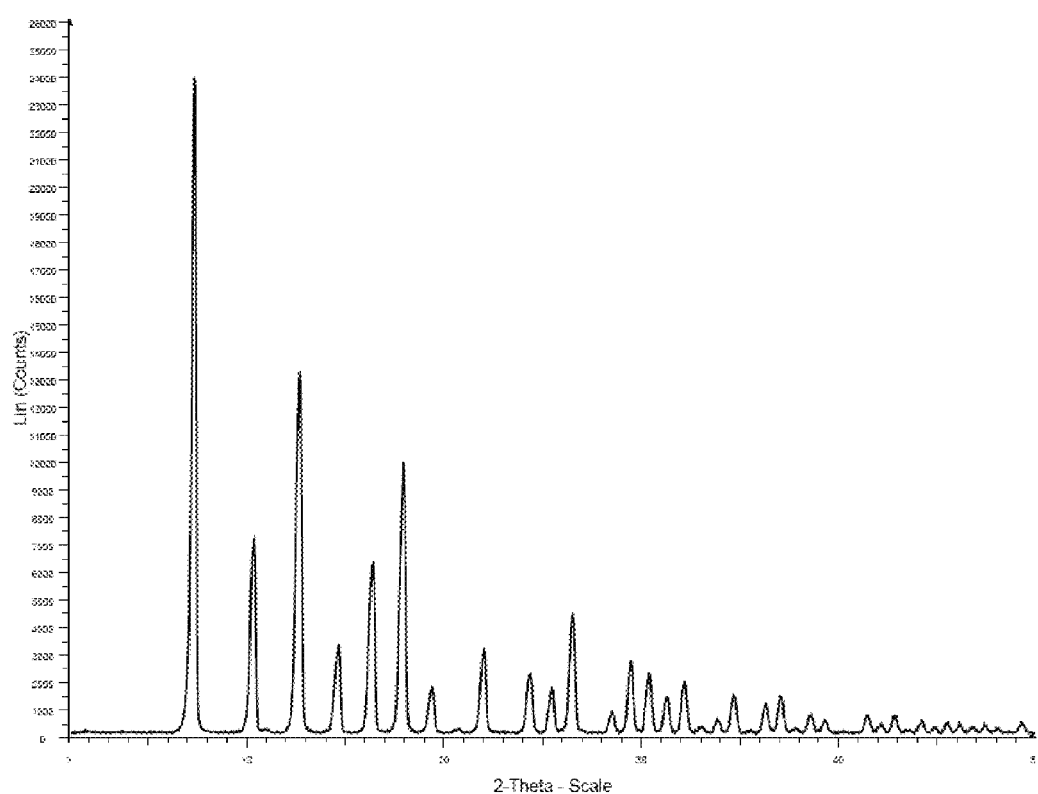
FIG. 26 shows PXRD pattern of ZIF-90 immersed in water for 18 h at room temperature.
Figure 27:
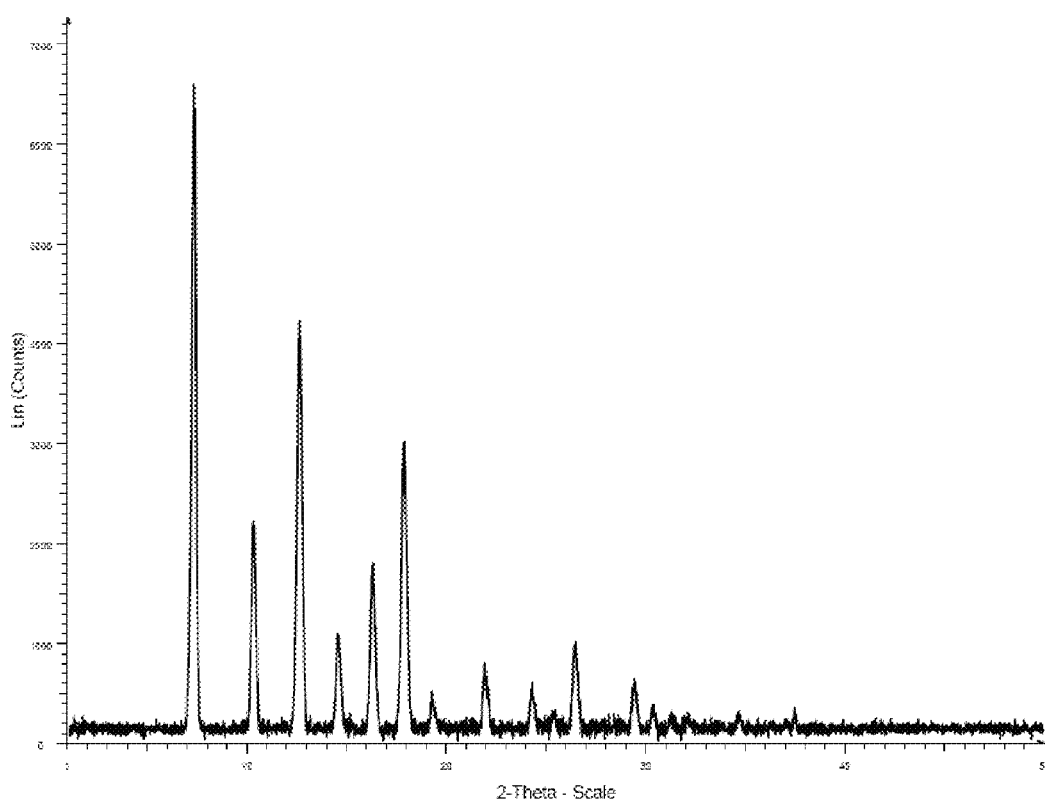
FIG. 27 shows PXRD pattern of ZIF-91 immersed in water for 24 h at room temperature.
Figure 28:
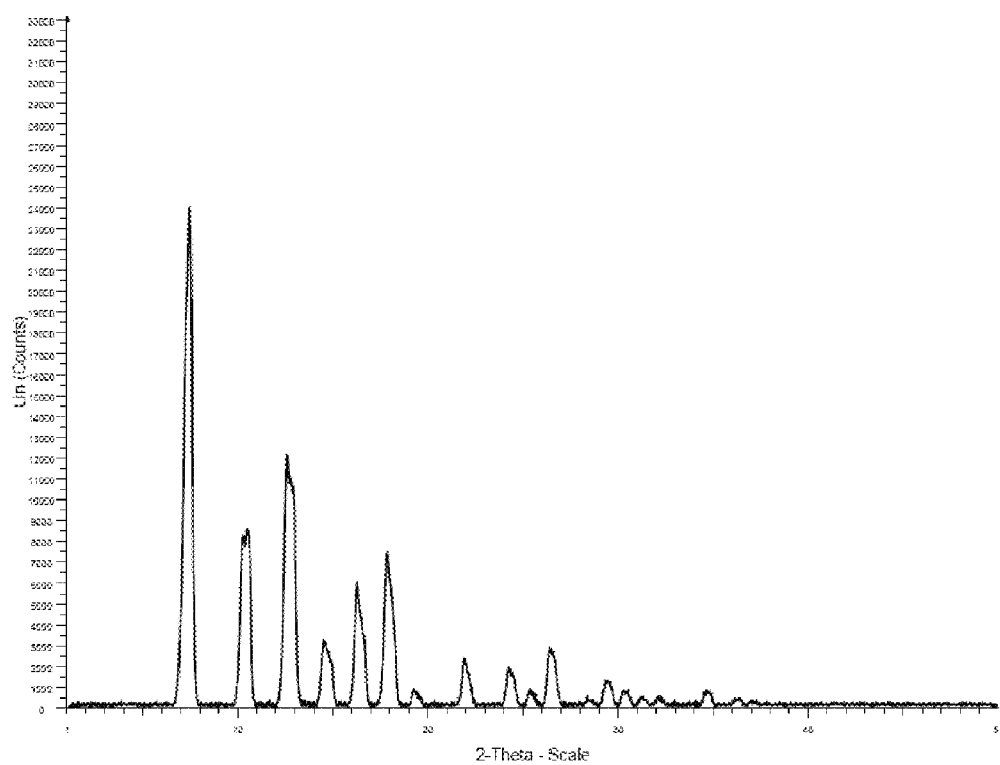
FIG. 28 shows PXRD pattern of ZIF-91 boiled in toluene for 18 h.
Figure 29:
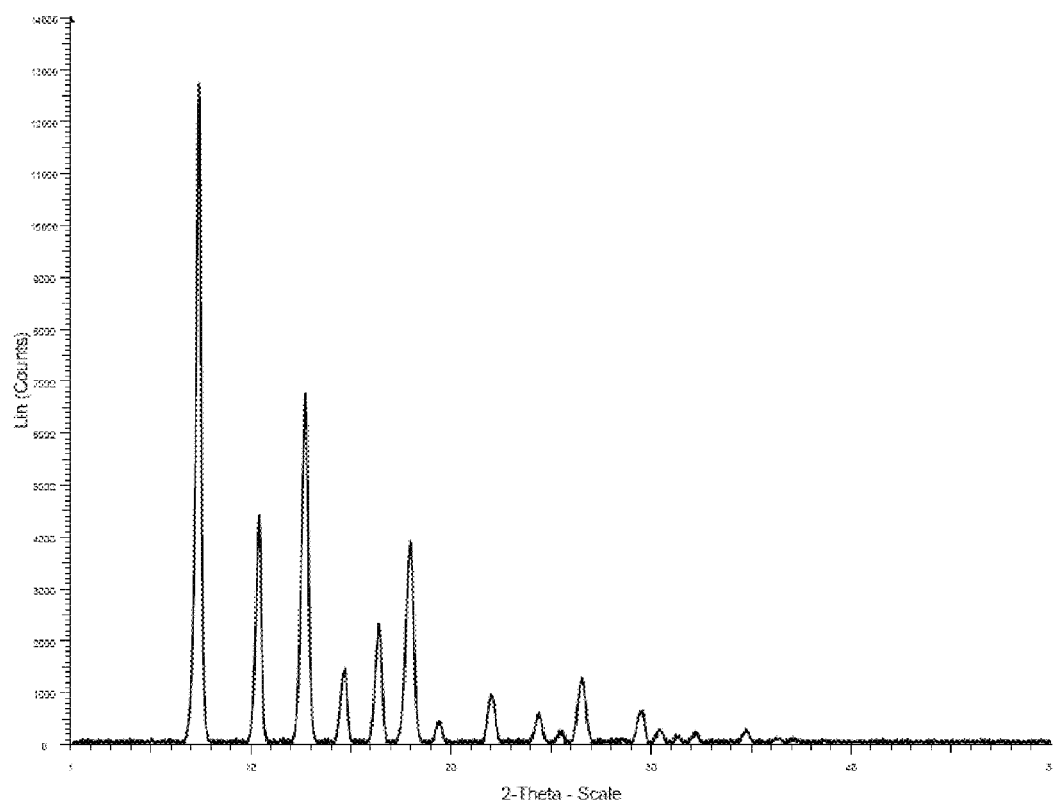
FIG. 29 shows a PXRD pattern of ZIF-91 boiled in MeOH for 18 h.
Figure 30:
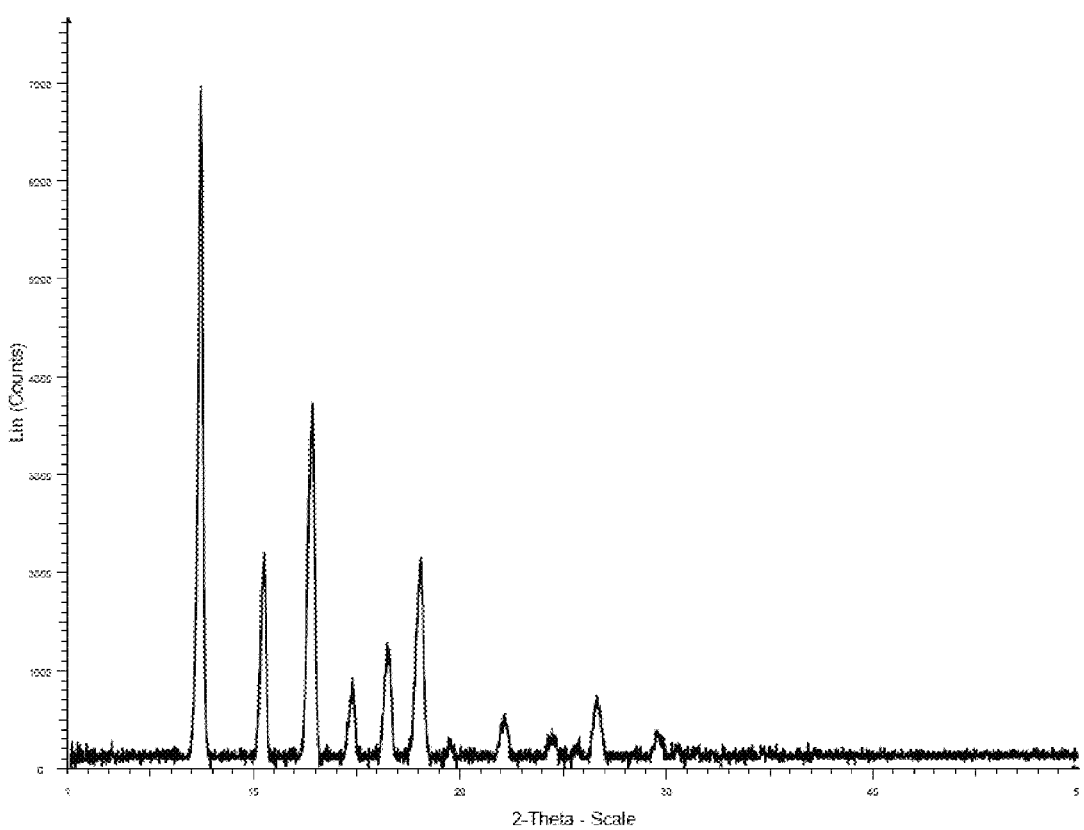
FIG. 30 shows a PXRD pattern of ZIF-91 heated to 200° C.
Figure 31:
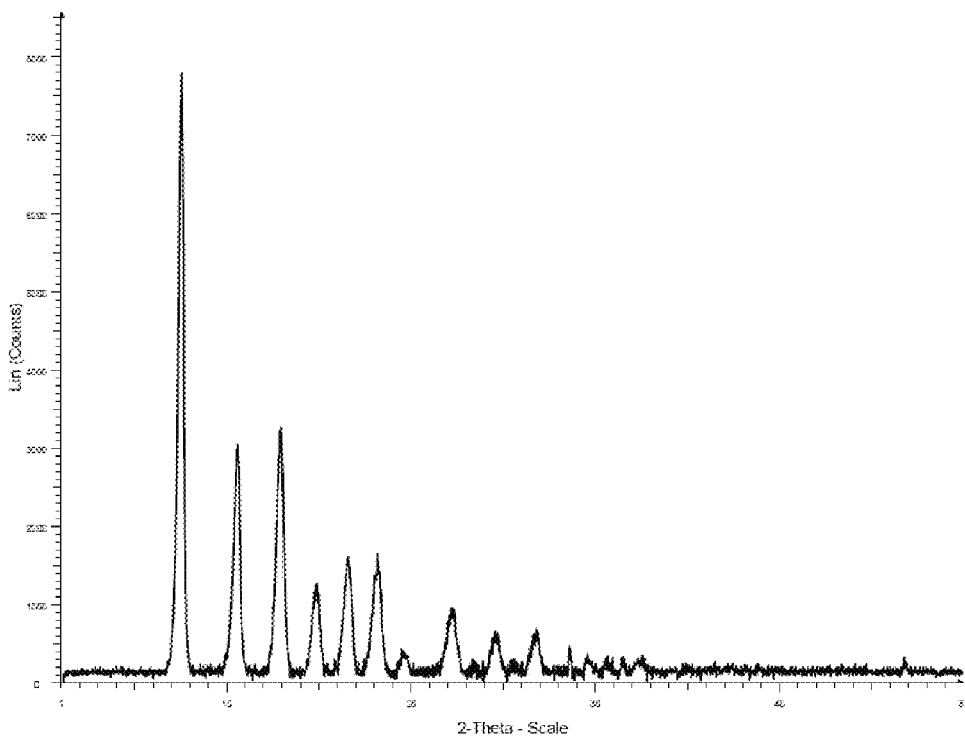
FIG. 31 shows a PXRD pattern of ZIF-92 heated to 100° C.
Figure 32:
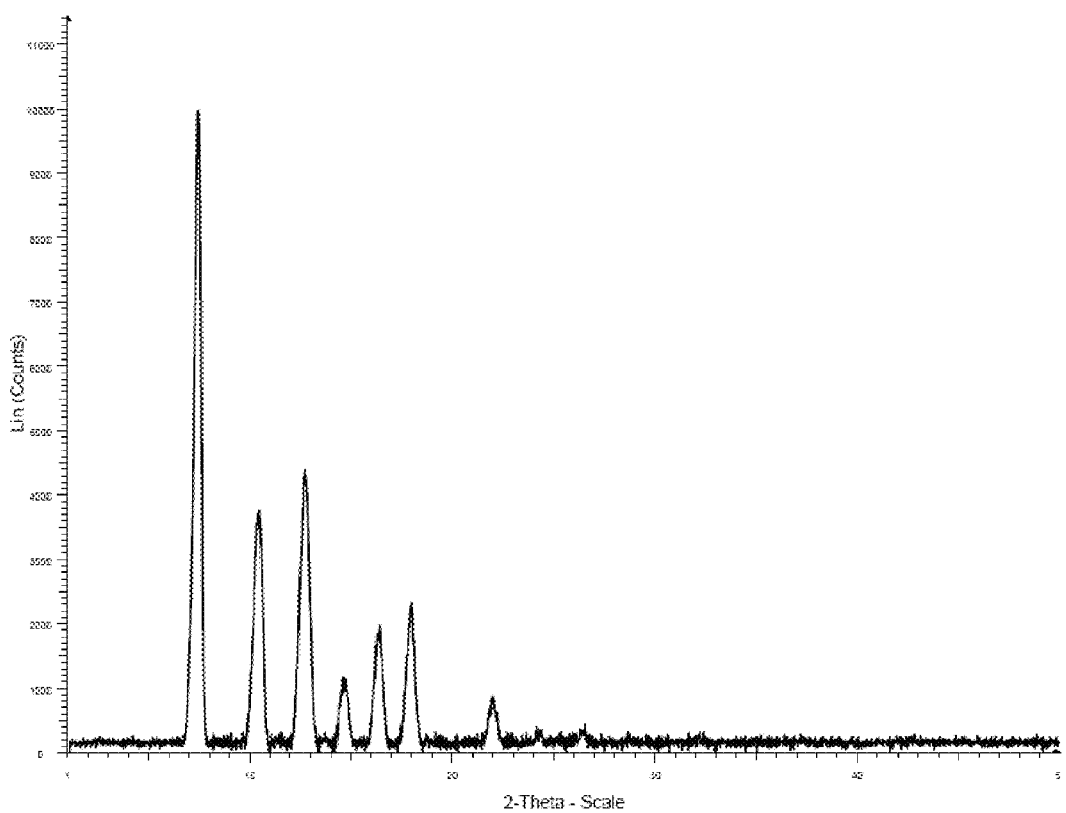
FIG. 32 shows a PXRD pattern of ZIF-92 boiled in toluene for 18 h.
Figure 33:
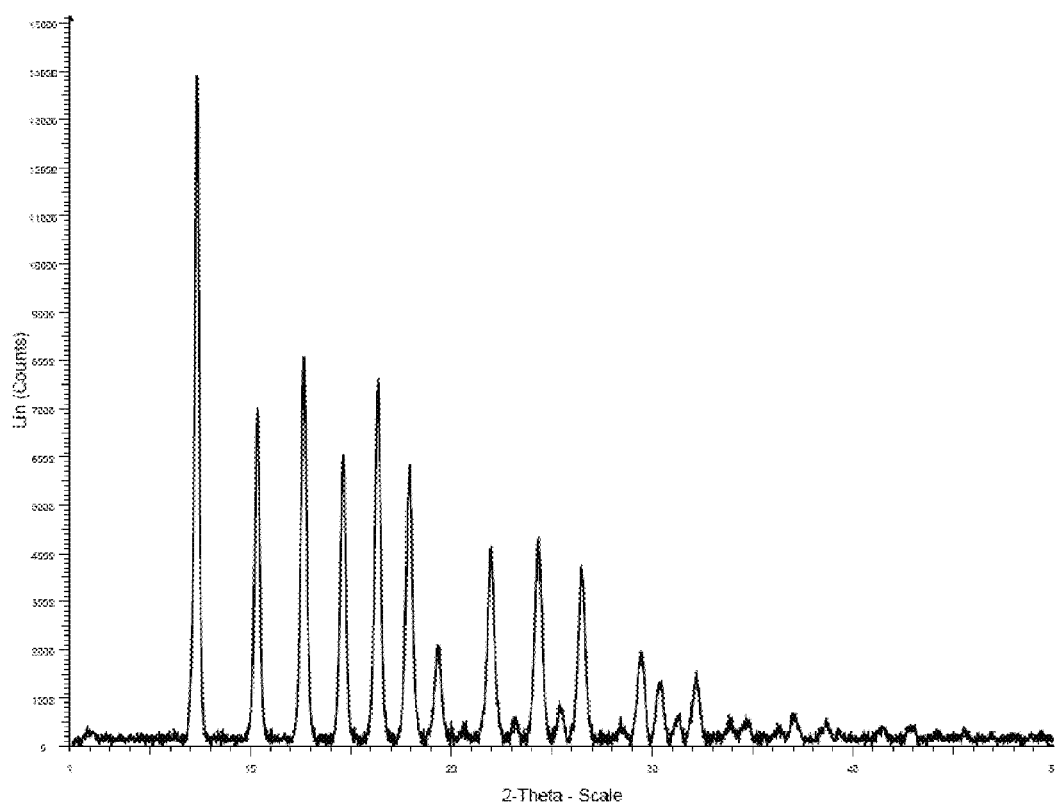
FIG. 33 shows a PXRD pattern of ZIF-92 boiled in MeOH for 18 h.
Figure 34:
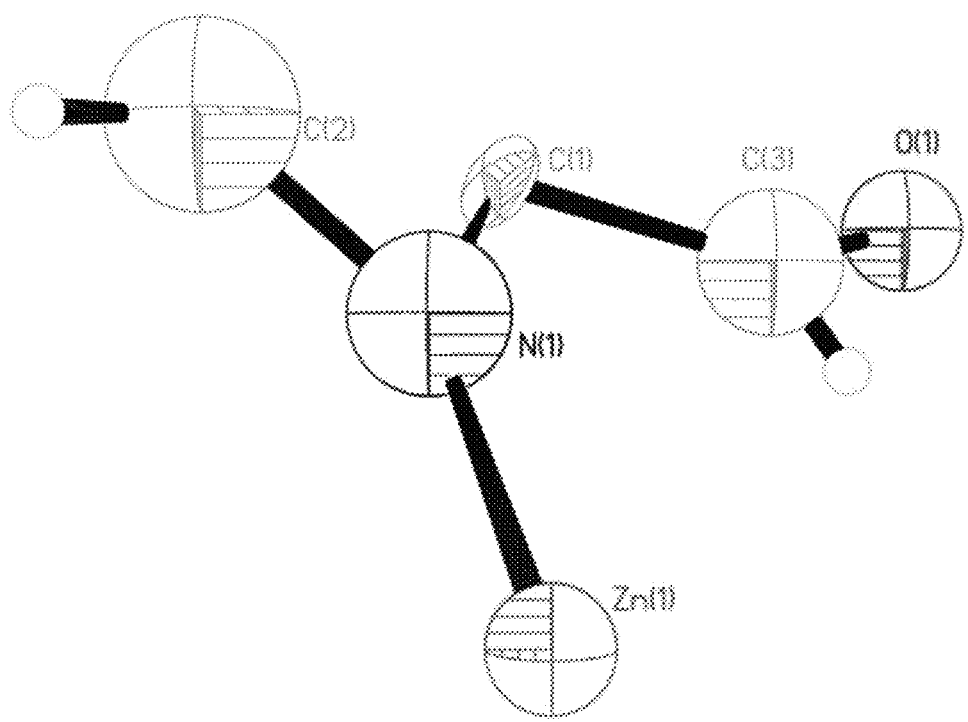
FIG. 34 shows an ORTEP drawing of asymmetric unit of ZIF-90.

Solution nuclear magnetic resonance (NMR) spectra were obtained at ambient temperature using a Bruker 400 MHz instrument. The signals are presented relative to TMS as 0 ppm using the water peak as a secondary reference at 4.79 ppm. ZIF-90 and ZIF-91 were digested in (20% DCl/D$_2$O), this allowed for quantification of reduction in ZIF-91. The relative integration of the aldehyde to alcohol peak in FIG. 16 showed 77.1% conversion of aldehyde to alcohol.

ESI Mass Spectrometry.

Mass spectrometry data shown for ZIF-91 digested in a formic acid/water (5%, v/v) solution. Peak at m/z of 95.20 corresponds to the negative parent ion of the 2-carboxaldehyde imidazole and the peak at 97.3 corresponds to the negative parent ion of the alcohol functionalized imidazole.

Gas Adsorption Measurements.

Low pressure gas adsorption isotherms were measured volumetrically on an Autosorb-1 analyzer (Quantachrome Instruments). A liquid nitrogen sample bath (77 K) was used for N$_2$, Ar, and H$_2$ isotherm measurements. The N$_2$, Ar, H$_2$ and He gases used were UHP grade. For measurement of the apparent surface areas (SLang), the Langmuir or BET method was applied using the adsorption branches of the N$_2$ isotherms assuming a N$_2$ cross-sectional area of 16.2 Å2/molecule. The total pore volumes (Vp) were determined using the Dubinin-Raduskavich (DR) method.

TABLE S1

Summary of the porosity of ZIFs

| Entry | Langmuir surface area/ $m^2 g^{-1}$ | BET surface area/ $m^2 g^{-1}$ | Total pore volume/ $cm^3 g^{-1}$ |
|---|---|---|---|
| ZIF-90 | 1320 | 1270[a] | 0.58 (0.48)[b] |
| ZIF-91 | 1070 | 1010[a] | 0.39 |

[a]See Walton, K. S. et al., JACS 2007. 129, 8552.
[b]Micropore volume.

Infrared Spectroscopy (IR).

FT-IR spectra of ZIF-90 and ZIF-92 were obtained as KBr pellets using Nicolet 400 Impact spectrometer, signals are given in wavenumbers (cm$^{-1}$).

Single Crystal X-Ray Diffraction Data Collection, Structure Solution and Refinement Procedures.

General Data Collection and Refinement Procedures: Data were collected on a Bruker SMART APEXII three circle diffractometer equipped with a CCD area detector and operated at 1200 W power (40 kV, 30 mA) to generate Cu Kα radiation (λ=1.5418 Å). The incident X-ray beam was focused and monochromated using Bruker Excalibur Gobel mirror optics. A crystal of ZIF-90 was mounted on a nylon CryoLoops (Hampton Research) with Paraton-N (Hampton Research).

Initial scans of each specimen were performed to obtain preliminary unit cell parameters and to assess the mosaicity (i.e. breadth of spots between frames) of the crystal to select the required frame width for data collection. In every case frame widths of 0.5° were judged to be appropriate and full hemispheres of data were collected using the Bruker APEX21 software suite to carry out overlapping φ and ω scans at three different detector (2θ) settings (2θ=28, 60, 100°). Following data collection, reflections were sampled from all regions of the Ewald sphere to redetermine unit cell parameters for data integration and to check for rotational twinning using CELL_NOW2. In no data collection was evidence for crystal decay encountered. Following exhaustive review of collected frames the resolution of the dataset was judged. Data were integrated using Bruker APEX2 V 2.13 software with a narrow frame algorithm and a 0.400 fractional lower limit of average intensity. Data were subsequently corrected for absorption by the program SADABS4. The absorption coefficient (μ) is 1.94 cm$^{-1}$ for the ZIF reported in this paper. However it is noteworthy that μ is based on the atomic contents and this is uncertain for most ZIF structures. The precise solvent molecule content is not known due to the diffuse electron density. The space group determination and tests for merohedral twinning were carried out using XPREP3. In all cases, the highest possible space group was chosen All structures were solved by direct methods and refined using the SHELXTL 975 software suite. Atoms were located from iterative examination of difference F-maps following least squares refinements of the earlier models. Final models were refined anisotropically (if the number of data permitted) until full convergence was achieved. Hydrogen atoms were placed in calculated positions (C—H=0.93 Å) and included as riding atoms with isotropic displacement parameters 1.2-1.5 times Ueq of the attached C atoms. Modeling of electron density within the voids of the frameworks did not lead to identification of guest entities in this structure due to the disordered contents of the large pores in the frameworks. The problem, which is typical for highly porous crystals that contain solvent filled pores, lies in the raw data where observed strong (high intensity) scattering becomes limited to ~1.0 Å at best, with higher resolution data sometimes present but weak (low intensity). A common strategy for improving X-ray data, increasing the exposure time of the crystal to X-rays did not improve the quality of the high angle data in this case, as the intensity from the low angle data saturated the detector and minimal improvement in the high angle data was achieved. Additionally, diffuse scattering from the highly disordered solvent in the void spaces within the crystal and from the loop used to mount the crystal contributes to the background noise and the 'washing out' of high angle data. The only optimal crystals suitable for analysis were generally small and weakly diffracting, and unfortunately, larger crystals, which would usually improve the quality of the data, presented a lowered degree of crystallinity and attempts to optimize the crystal growing conditions for large high-quality specimens has not yet been fruitful. For ZIF-90, it was found that data collection at −173° C. was optimal for obtaining the best data. In such cases the modeling of the disordered guest entities becomes intractable because at the lower temperature they become frozen into highly disordered arrays. Thus, electron density within void spaces, which could not be assigned to any definite guest entity, was modeled as isolated oxygen and/or carbon atoms, and the foremost errors in all the models lies with assignment of guest electron density. To prove the correctness of the atomic positions in the framework the application of the SQUEEZE6 routine of A. Spek had been performed. The assignment and refinement of the metal-organic ZIF framework atoms was unambiguous, as judged by the resulting bond and angle metrics which are chemically accurate and precise values. All structures were examined using the Adsym subroutine of PLATON7 to assure that no additional symmetry could be applied to the models. All ellipsoids in ORTEP diagrams are displayed at the 30% probability level unless noted otherwise. For all structures we note that the elevated R-values are commonly encountered in MOF crystallography, for the reasons expressed above, by us and other research groups 8-17 ZIF-90 (SOD—Cubic).

Experimental and Refinement Details for ZIF-90. A red colored cubic crystal (0.18×0.16×0.16 mm3) of ZIF-90 (CCDC693596) was placed in a 0.7 mm diameter nylon CryoLoops (Hampton Research) with Paraton-N (Hampton Research). The loop was mounted on a SMART APEXII three circle diffractometer equipped with a CCD area detector and operated at 1200 W power (40 kV, 30 mA) to generate Cu Kα radiation ($\lambda$=1.5418 Å) while being flash frozen to 100(2) K in a liquid N2 cooled stream of nitrogen. A total of 6067 reflections were collected of which 317 were unique and 308 of these were greater than 2σ(I). The range of θ was from 1.91 to 40.66°. Analysis of the data showed negligible decay during collection. The structure was solved in the cubic I-43 m space group, with Z=2, using direct methods. Atom Zn1 was refined anisotropically. All other non-hydrogen atoms were refined isotropically with hydrogen atoms generated as spheres riding the coordinates of their parent atoms. ZIF-90 is composed of two 2-imidazole carboxaldehyde linker per Zn. The attempts made to model the guests (solvent molecules) did not lead to identification of guest entities in this structure due to the limited periodicity of the solvent molecules in the crystals. Since the solvent is neither bonded to the framework nor tightly packed into the voids, solvent disorder can be expected for the MOF structures. Thus, electron density within void spaces which could not be assigned to any definite guest entity was modeled as isolated carbon atoms, and the foremost errors in all the models lies with the assignment of guest electron density. To assess the correctness of the atomic positions in the framework, the application of the SQUEEZE routine of A. Spek has been performed. It should be noted that the precision of this model is low; however, the structure is reported to display the framework for ZIF-90 as isolated in the crystalline form. Other supporting characterization data (vide infra Materials and Methods) are consistent with the crystal structure. Final full matrix least-squares refinement on F2 converged to R1=0.1447 (F>2σF)) and wR2=0.3497 (all data) with GOF=1.832. When only framework atoms are included in the latter structure factor calculation, the residual electron density in the F-map is located within the pores of ZIF-90.

TABLE S2

| Crystal data and structure refinement for ZIF-90. | |
|---|---|
| Empirical formula | 'C8H6N4O2Zn1' |
| Formula weight | 255.55 |
| Temperature | 100(2) K |
| Wavelength | 1.54178 Å |
| Crystal system | Cubic |
| Space group | I-43 m |
| Unit cell dimensions | a = 17.2715(4) Å α = 90° |
| | b = 17.2715(4) Å β = 90° |
| | c = 17.2715(4) Å γ = 90° |
| Volume | 5152.2(2) |
| Z | 2 |
| Density (calculated) | 0.988 |
| Absorption coefficient | 1.936 |
| F(000) | 1728 |
| Crystal size | 0.18 × 0.16 × 0.16 mm$^3$ |
| Theta range for data collection | 1.95-39.61 |
| Index ranges | −14 <= h <= 14, −13 <= k <= 14, −14 <= l <= 13 |
| Reflections collected | 6748 |
| Independent reflections | 317 [Rint = 0.0297] |
| Completeness to theta = 39.61° | 100.00% |
| Absorption correction | Semi-empirical from equivalents |
| Refinement method | Full-matrix least-squares on F$^2$ |
| Data/restraints/parameters | 317/2/26 |
| Goodness-of-fit on F$^2$ | 1.836 |
| Final R indices [I > 2sigma(I)] | R$_1$ = 0.1447, wR$_2$ = 0.3474 |
| R indices (all data) | R$_1$ = 0.1455, wR$_2$ = 0.3497 |
| Largest diff. peak and hole | 0.862 and −1.325 e · Å$^{-3}$ |

The disclosure shows that useful organic transformations can be performed on crystalline frameworks (e.g., ZIFs) without altering the original structural integrity. The fact that these reactions proceed to high conversions under the same reaction conditions required in solution realizes the idea of "crystals as molecules". Indeed the high porosity and openness of the ZIF structures provide the medium for these reactions and allow for chemical transformations to take place in precise and well-defined spatial arrangements.

What is claimed is:

1. A method of generating a post-reactive framework (PRF) comprising:
    generating a porous framework comprising a ZIF, a COF, a MOF or a BOF wherein a linking moiety of the porous framework comprises one or more reactive side groups selected from the group consisting of NH$_2$, CN, OH, =O, =S, SH, P, Br, CL, I, F,

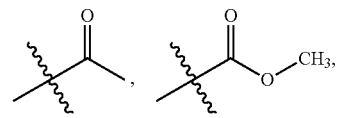

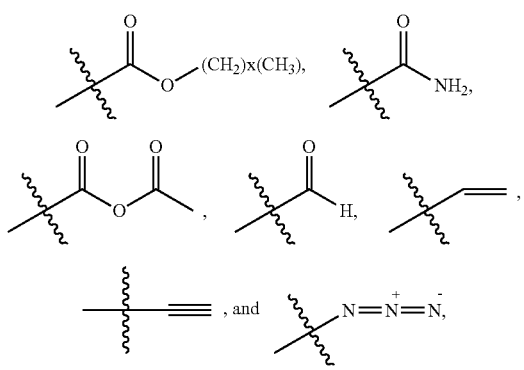

wherein X=1, 2, or 3; and reacting the framework with a post framework reactant comprising a heterocyclic compound under conditions wherein the post framework reactant modifies the reactive side group to form a PRF.

2. The method of claim 1, wherein the porous framework comprises a general structure M-L-M, wherein the M is a transition metal and L is a linking moiety.

3. The method of claim 2, wherein L comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings and a linking cluster covalently bound to the substructure.

4. The method of claim 2, wherein the linking moiety is selected from the group consisting of:

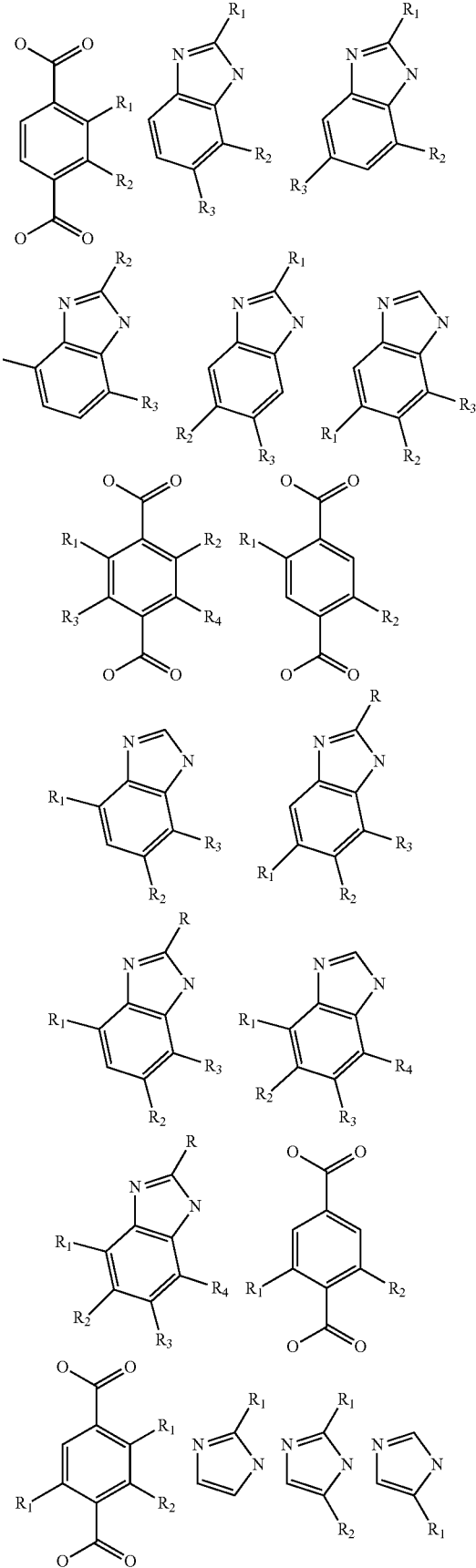

-continued

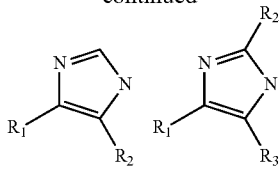

wherein $R_1$, $R_2$, $R_3$, $R_4$=NH$_2$, CN, OH, =O, =S, SH, P, Br, CL, I, F,

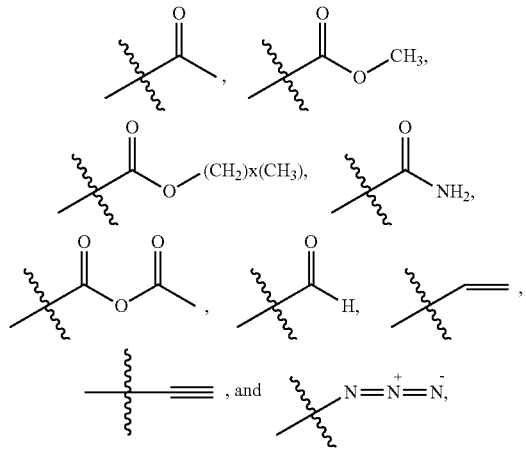

wherein X=1, 2, or 3.

5. The method of claim 1, further comprising a metal or metal containing compound that chelates to and adds functional groups to the reactive side group.

6. The method of claim 5, wherein the post framework reactant undergoes reaction with the porous framework that results in the tethering of organometallic complexes to the framework.

7. The method of claim 1, wherein the heterocyclic compound has one or more multivalent heteroatoms, independently selected from N, O and S, as a part of the ring structure.

8. The method of claim 7, wherein the heterocyclic compound comprises a monocyclic heterocycle.

9. The method of claim 8, wherein the monocyclic heterocycle is selected from the group consisting of: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

10. The method of claim 8, wherein the heterocycle is selected from the group consisting of:

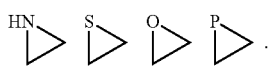

11. The method of claim 1, wherein the reaction is carried out with reagents that result in a modification of a reactive side group so that the modified reactive side group extends into the pore of the framework thereby modifying pore size or charge.

12. The method of claim 1, wherein the post reactive framework comprises a modification of the linker moiety comprising an aliphatic sulfonic acid group.

13. The method of claim 1, wherein a guest species is removed from the porous framework prior to reacting the framework with the post framework reactant.

14. A method of generating post-reactive framework (PRF) comprising:
generating a porous framework comprising a ZIF, a COF, a MOF or a BOF wherein a linking moiety of the porous framework comprises one or more reactive side groups selected from the group consisting of secondary or tertiary amine, CN, OH, =O, =S, SH, P, Br, CL, I, F,

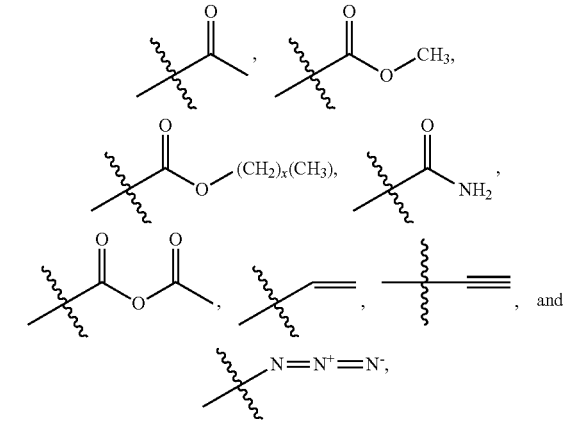

wherein X=1, 2, or 3; and
reacting the framework with a post framework reactant comprising a heterocyclic compound under conditions wherein the post framework reactant modifies the reactive side group to form a PRF.

15. The method of generating post-reactive framework (PRF) of claim 14, wherein:
the linking moiety of the porous framework comprises one or more reactive side groups selected from the group consisting of CN, OH, =O, =S, SH, P, Br, CL, I, F,

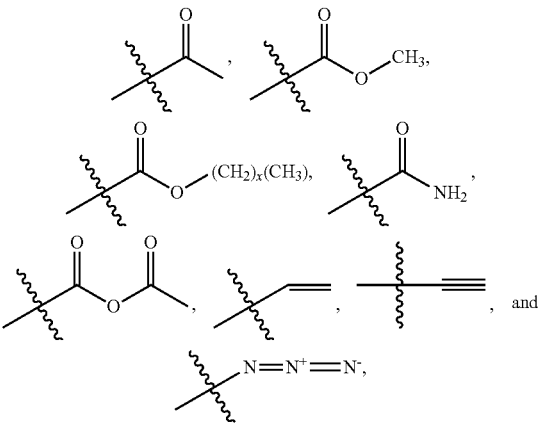

wherein X=1, 2, or 3.

16. The method of generating post-reactive framework (PRF) of claim 14, wherein:
   reacting the framework with a post framework reactant comprising the heterocyclic compound under conditions wherein the post framework reactant substitutes for the reactive side group to form a PRF.

17. The method of generating post-reactive framework (PRF) of claim 14, wherein:
   reacting the framework with a post framework reactant comprising the heterocyclic compound under conditions wherein the post framework reactant adds to the reactive side group to form a PRF.

18. The method of generating post-reactive framework (PRF) of claim 14, wherein:
   reacting the framework with a post framework reactant comprising the heterocyclic compound under conditions wherein the post framework reactant adds to the reactive side group and then the reactive side group is eliminated to form a PRF.

\* \* \* \* \*